United States Patent
Kominami et al.

(10) Patent No.: US 6,645,734 B2
(45) Date of Patent: Nov. 11, 2003

(54) SERINE PROTEASE SPECIFIC MONOCLONAL ANTIBODIES AND THEIR USE

(75) Inventors: Katsuya Kominami, Hannan (JP); Akira Okui, Yamatokoriyama (JP); Shinichi Mitsui, Kyoto (JP); Nozomi Yamaguchi, Kyoto (JP)

(73) Assignee: Fuso Pharmaceutical Industries, Ltd., Osaka (JP)

(*) Notice: Subject to any disclaimer, the term of this patent is extended or adjusted under 35 U.S.C. 154(b) by 191 days.

(21) Appl. No.: 09/741,171

(22) Filed: Dec. 21, 2000

(65) Prior Publication Data

US 2001/0016331 A1 Aug. 23, 2001

Related U.S. Application Data

(63) Continuation-in-part of application No. PCT/JP99/03578, filed on Jul. 2, 1999.

(30) Foreign Application Priority Data

Jul. 2, 1998 (JP) .......................................... 10/187506

(51) Int. Cl.[7] ...................... G01N 33/53; G01N 33/573; G01N 33/577; C07K 16/40; C12N 5/20

(52) U.S. Cl. ...................... 435/7.92; 435/7.1; 435/7.23; 435/7.4; 435/7.94; 435/7.95; 435/23; 435/40.52; 435/226; 435/332; 435/338; 435/960; 436/503; 436/518; 436/548; 436/63; 436/164; 436/811; 530/388.2; 530/388.26; 530/391.3

(58) Field of Search ................................ 435/7.1, 7.23, 435/7.4, 7.92, 7.94, 23, 226, 452, 328, 332, 338, 7.95, 960, 40.52; 436/503, 518, 548, 63, 811, 164; 530/387.3, 388.2, 388.26, 391.3

(56) References Cited

U.S. PATENT DOCUMENTS 5,733,768 A   3/1998 Dixon et al. ................. 435/226

FOREIGN PATENT DOCUMENTS

| EP | 576152 | 12/1993 |
|---|---|---|
| JP | 6-62855 | 3/1994 |
| JP | 9-149790 | 6/1997 |
| WO | WO 98/11238 | 3/1998 |

OTHER PUBLICATIONS

Petraki et al., 2001. The Spectrum of human kallikrein 6 (Zyme/Protease M/Neurosin) expression in human tissues as assessed immunohistochemistry. Journal of Histochemistry & Cytochemistry 49(11):1431–41.*
Campbell, 1984. *Monoclonal Antibody Technology*, Elsevier, Amsterdam, pp. 1–4 and 29.*
Harlow et al., 1988. *Antibodies. A Laboratory Manual*, Cold Spring Harbor Laboratory, Cold Spring Harbor. Pp. 72–77.*
Maurer et al., 1980. Proteins and polypeptides as antigens. Meth. Enzymology 70:49–70.*
Yamashiro, K., et al., Biochimica et Biophysica Acta 1350, 11–14 (1997).
Little, S. P., et al., J. Biol. Chem. 272, 25135–25142 (10/97).

* cited by examiner

*Primary Examiner*—Christopher L. Chin
*Assistant Examiner*—James L. Grun

(57) ABSTRACT

A monoclonal antibody binding selectively to neurosin obtained from hybridomas, in particular, strain 2B2-6 and strain S2E5 showing stable proliferation ability. These hydridomas are obtained by fusing mouse spleen cells having a high antibody titer against neurosin with mouse-derived myeloma cells, screening fused cells being highly reactive with neurosin, and thus producing an antibody binding specifically to neurosin. By using this antibody, various diseases in which neurosin participates can be diagnosed.

13 Claims, 12 Drawing Sheets

1: recombinant neurosin
2: trypsinogen
3: HPC-Y3 culture supernatant (100-fold concentrated)
4: CSF

|   |         |      | CSF neurosin level (by ELISA) |
|---|---------|------|-------------------------------|
| 1;| CSF 1-8 | 1-8  | 1.80 (μg/ml)                  |
| 2;| CSF 1-9 | 1-9  | 2.00                          |
| 3;| CSF 1-18| 1-18 | 0.39                          |
| 4;| CSF 1-14| 1-14 | 3.20                          |
| 5;| CSF 1-15| 1-15 | 2.50                          |
| 6;| CSF 1-4 | 1-4  | 0.13                          |
| 7;| CSF 1-33| 1-33 | 0.20                          |
| 8;| CSF 1-34| 1-34 | 0.28                          |
| 9;| CSF 1-17| 1-17 | 0.18                          |

FIG. 5

Electrophoresis pattern and immunostaining of purified CSF-derived neurosin
  A. Silver staining
  B. Immunostaining

FIG. 7

Neurosin         MKKLMVVLSLIAAAWAEEQNKLVHGGPCDKTSHPYQAALY....
                                 ↑Pro-form
Mature neurosin                  LVHGGPCDKTSHPYQAALY....

CSF-derived neurosin    EEQNKLVHGGPCDK

N-terminus amino acid sequence of CSF-derived neurosin

W: Homogenate fraction

C: Cell sol fraction

M: Membrane fraction

SERINE PROTEASE SPECIFIC MONOCLONAL ANTIBODIES AND THEIR USE

PRIORITY INFORMATION

This is a continuation-in-part of PCT/JP99/03578 filed on Jul. 2, 1999 which claims convention priority from Japanese Patent Application Number 187506/1998, filed Jul. 2, 1998; PCT/JP99/03578 has been published under No. WO 00/01807 and the publication is not in English. A Demand for Chapter II was filed in PCT/JP99/03578.

BACKGROUND OF THE INVENTION

1. Field of the Invention

The present invention relates to monoclonal antibodies binding specifically to a certain serine protease, i.e., neurosin. It also relates to a production process thereof and a method for diagnosing various diseases using the monoclonal antibodies.

2. Disclosure of the Prior Art

In general, proteases are biosynthesized as inactive precursors. They undergo limited hydrolysis in molecules to convert into activated type proteases. In so far as enzymes are proteases, they have an activity for hydrolyzing a peptide bond. However, their action modes are varied according to kinds of proteases. According to particular kinds of catalytic sites, proteases are divided into serine proteases, cysteine proteases, aspartate proteases, metal proteases and the like. Proteases of each kind have a variety of properties such as, from that having general digestive properties to that having various regulatory domains and strict substrate specificity, thereby specifically hydrolyzing only characteristic proteins.

The optimal pH range of serine proteases is neutral to weak alkaline and, in general, many of them have a molecular weight of about 30,000 or lower. All proteases of blood coagulation, fibrinolysis and complement systems which have a large molecular weight belong to trypsin-like serine proteases. They have many regulator domains and form a protease cascade which is very important to reactions in a living body.

According to their primary structure, serine proteases can be divided into subtilisin family and chymotrypsin family. Those of subtilisin family are produced by only *Bacillus subtilis,* while those of chymotrypsin family are widespread in microorganisms, animals and plants. His-57, Asp-102 and Ser-195 (chymotrypsin Nos.) are concerned in their catalytic activity and, in general, they are inactivated by diisopropyl fluorophosphate (DFP). For exhibiting their activity, a catalytic triad is required, in which His influenced by Asp deprives Ser-195 of its proton to activate Ser. Further, it binds to a substrate to cause polarization of the carbonyl group, and the oxygen atom forms oxy anion. Trypsin has Asn-189 at this site and interacts with the positive charge of a basic amino acid such as Lys, Arg or the like. On the other hand, the corresponding site of chymotrypsin is Ser-189, and an aromatic amino acid such as Tyr, Phe, Trp or the like, or Leu or Met can also bind thereto. In analogy with chymotrypsin, esterase has Ser-189 and interacts with a non-aromatic amino acid such as Ala or the like. As other enzymes belonging to chymotrypsin family, there are Achromobacter protease, plasmin, medullasin, acrosin, V8protease, cathepsin G, chymase, proline specific endopeptidase, submaxillary gland protease A, XIIa, XIa, plasma kallikrein, IXa, Xa, α-thrombin, VIIa, protein C, tissue plasminogen activator, urokinase, C1r, C1s, C2, B, D, I, γ-seminoprotein, tissue kallikrein, C and B factors of *Limulus polyphemus* blood cells, blood coagulation enzymes and the like.

Recently, cDNA and amino acid sequences of many novel proteases have been determined by PCR using oligonucleotide primers for consensus sequences of serine proteases. According to this method, novel proteases have been found by various researchers such as Yamamura et al. (Yamanura, Y et al., Biochem. Biophys. Res. Commun., 239, 386, 1997), Gschwend, et al. (Gschwend, T. P. et al., Mol. Cell. Neurosci., 9. 207, 1997), Chen et al. (Chen, Z-L, et al., J. Neurosci., 15, 5088, 1995) and others.

SEQ ID NO: 3 of JP 9-149790 A discloses neurosin as a novel serine protease. Neurosin has also been reported in Biochimica et Byophysica Acta, 1350, 11–14, 1997. Neurosin having not more than 30% identity to known serine proteases has been obtained as a result of recognition of serine protease activity in a culture supernatant of human colon cancer COLO201 cells and isolation of a cDNA encoding neurosin. By this, there is provided a method for mass production of neurosin using the serine protease gene and a method for screening specific inhibitors using the enzyme. In addition, the screening method has been shown to be useful for screening medicines for treating various diseases.

At present, functions of neurosin are still unknown. However, since neurosin is abundantly expressed in brain, it is presumed to play an important role in maintenance of brain functions. Further, there is a possibility that further detailed functions can be elucidated by using recombinant protein.

JP 6-62855 A discloses a novel serine protease, Zyme, and this is also reported by J. Biol. Chem., 272(40), 25135–2514, 1997. The cDNA and amino acid sequences of Zyme have been determined by PCR amplification of consensus sequences having chymotrypsin-like activity to construct a cDNA library by using the brain mRNA of a patient with Alzheimer's disease. The mRNA encoding Zyme is recognized in several mammals. Further, although Zyme is expressed abundantly in brain, kidney and salivary glands, as to brain, it is not expressed in fetal brain, but is expressed only in adult brain. Further, Zyme has a gene in chromosome 19q13.3, and this region has been revealed to be a part linking to late onset familial Alzheimer's disease. Then, it is considered that Zyme would be useful for elucidating characteristics of neural diseases such as Alzheimer's disease and Down's syndromes.

WO 98/11238 discloses a novel protease, Protease M, and this is also reported in Molecular Medicine, 2(5), 624–636, 1996. Protease M cDNA is obtained from normal human mammary epithelial 76 N cell line and has a sequence very similar to kallikrein, Prostate-Specific Antigen (PSA) and trypsin. And, Protease M gene is present in chromosome 19q13.3. Protease M is considered to be a marker useful for primary breast adenocarcinoma and primary ovary cancer because, while it is downregulated in metastatic breast cancer cell line, its mRNA is strongly expressed in primary breast cancer cell line, ovary cancer tissue and cancer cell line.

Although origins of these neurosin, Zyme and Protease M are different, their cDNA sequences and amino acid sequences, and further the positions in chromosome conformation of the genes encoding them are completely identical to one another. Since there is a high possibility that these substances would be the same substance, the name "neurosin" is used herein to refer to them altogether. As described above, this serine protease has been found by different groups of researchers almost at the same time, and its pharmacological activities have been studied. Then, it is expected that its importance will be elucidated on various occasions in the future. For example, Games et al. (Games, D. et al., Nature, 373, 523, 1995) and Hsiao et al. (Hsiao, K, et al., Science, 274, 99, 1996) succeeded in expression of a large amount of β-amyloid precursor protein (βAPP), and production of transgenic mice in which deposition of amyloid β protein (Aβ) was observed in 1995 and 1996, respectively. Then, the role of the above serine protease in Alzheimer's disease and the like will be further elucidated in the future.

As disclosed in JP 6-62855 A, Zyme (i.e., neurosin) plays an important role in Alzheimer's disease and Down's syndromes. While it has been proposed that Alzheimer's disease should be divided into that presenile Alzheimer's disease and Alzheimer type senile dementia manifesting in senescence from the pathological viewpoint, the term "Alzheimer's disease" is used herein to refer to them altogether.

Clinically, Alzheimer's disease is characterized by progressive decline of various recognition functions and the main neuropathological observation is to find abnormal structures such as senile plaque and neurofibril change in addition to nerve cell degeneration and deficiency (Trojanowski, J. Q. et al., In Current Neruology, 16, 93, 1996). Among them, while senile plaque also appears in case of normal aging, it appears much more frequently in case of Alzheimer's disease and is a pathological observation having high disease specificity. Further, β-amyloidogenesis can be said to be a most important subject to be elucidated from the pathogenic viewpoint because, for example, the deposition of Aβ which is a constituent component of senile plaque is the earliest pathological observation in brain of Alzheimer's disease, and further familial Alzheimer's disease having point mutation in βAPP gene which is the precursor of Aβ has been found.

In Down's syndromes wherein the 21st chromosome having βAPP is a trisomy, the same pathological observation in brain as that of Alzheimer's disease is found in all cases after age thirty. Teller et al. (Teller, J. K. et al., Nature Med., 2, 93, 1996) have reported that soluble Aβ1-42 increases in proportion to age and density of senile plaque on the basis of the results of determination of soluble Aβ extracted from brains of patients with Down's syndrome, aged from fetal to in their sixties, by immunoprecipitation and western blotting. In addition, they have suggested that the increase in soluble Aβ is concerned with excess production of βAPP and formation of senile plaque because soluble Aβ is found even in cases of juvenile Down's syndrome wherein no senile plaque is present, while it is not observed in a control group. Further, Tokuda et al. (Tokuda, T. et al., Ann. Neurol., 41, 271, 1997) have reported that the significant increase in both plasma Aβ1-40 and Aβ1-42 (43) in a group with Down's syndrome is found in comparison with that of a control group. In view of these facts, there is a possibility that neurosin would have a certain action on Down's syndrome.

Further, neurosin is also considered to have a certain action on dementia pugilistica and diffuse Lewy bodies disease which are closely related to Alzheimer's disease.

Senile plaque is a spot structure having 50 to 200 μm diameter which mainly appears in cerebral cortex of brain with Alzheimer's disease. Senile plaque after passage of time has an amyloid core in the center and accumulation of degenerated axons and reactive glia cells are observed about it. Aβ is polymerized in the form of a β sheet structure to form amyloid fiber. In general, it is considered that the extracellularly polymerized amyloid Aβ is toxic to nerve cells (Yankner, B. A. et al., Science, 250, 279, 1990; Simmons, L. K. et al., Mol. Pharmacol., 45, 373, 1994). Aβ is a main component of the amyloid core which has a molecular weight of about 4 kDa and is composed of about 42 amino acids. In addition to senile plaque, it accumulates in small blood vessels in meninx and cortex to form amyloid angiosis. Kang et al. (Kang et al., Nature, 325, 733, 1987) have showed that Aβ is derived from the larger precursor, βAPP, by cloning based on the information of the amino acid sequence of Aβ revealed by Glenner et al. (Glenner, G. G. and Wong, C. W., Biochem. Biophys. Res. Commun., 120, 185, 1984).

βAPP is a glycoprotein having a structure similar to that of a transmembrane receptor and having a molecular weight of 120,000 to 130,000. Aβ is integrated in the region from the transmembrane domain through the extracellular domain of βAPP. At present, 6 kinds of βAPP have been identified. As the identified βAPP which is concerned in amyloid deposition, there are βAPP659 which is predominantly expressed in brain (Kang, J. et al., Proc. Natl. Acad. Sci., 82, 4245, 1985), βAPP751 which has an amino acid region composed of 56 amino acids homologous to a serine protease inhibitor of Kuntiz family, βAPP770 which has an amino acid region composed of 19 amino acids homologous to MRC X-2 antigen, and the like. βAPP751 and βAPP770 are predominantly expressed in whole body organs. Since all of them have Aβ part at the 99th amino acid from the C-terminus, they are considered to be concerned in amyloid formation in brain.

While physiological functions of βAPP are still unknown, βAPP expressed in cell surfaces, or soluble βAPP which are cleaved in Aβ domain and released from cells has been reported to act extracellularly as a cell adhesion molecule (Schubert, D. and Behl, C., Brain Res., 629, 275, 1993), or a certain nutriment factor (Saitoh, T. et al., Cell, 58, 615, 1989). On the other hand, βAPP is presumed to be carried to the end of axon with an axonal flow, followed by expression in synaptic membrane, thereby playing an important role in synapse formation or its maintenance in nerve cells (Schubert, W. et al., Brain Res., 563, 184, 1991).

As to metabolism of βAPP, in general, two pathways are presumed. That is, one is a secretion pathway wherein Aβ domain is cleaved at the center thereof with so-called α-secretase and its N-terminus product is released to outside of cells. The other is endosomal-lysosomal pathway wherein βAPP is incorporated in cells directly or after once expressed on cell surfaces and, finally, it is decomposed in lysosomes. Although the region in which Aβ is produced during these βAPP metabolism pathways is still unknown, one possibility which can be presumed is that Aβ is cut out immediately after incorporation of βAPP in endocytic vesicle and is released to outside of cells immediately (Koo, E. H. and Squazzo, S. L., J. Biol. Chem., 269, 17386, 1994).

After discovery of Aβ, it was considered that cut out of Aβ was caused only in a disease state. However, the later studies have revealed that Aβ is produced physiologically and is present in the soluble state in a culture supernatant (Haass, C. et al., Nature, 359, 322, 1992; Shoji, M. et al., Science, 258, 126, 1992) or in cerebrospinal fluid (Shoji, M. et al., Science, 258, 126, 1992; Seubert, P. et al., Nature, 359, 325, 1992). For cutting out of Aβ from βAPP, an enzyme for cleaving the N-terminus side of Aβ (β-secretase) and an enzyme for cleaving the C-terminus side of Aβ (γ-secretase) are required (Haass, C. et al.; Cell, 75, 1039, 1993). While these secretases of Aβ are not yet identified, recently, it has been revealed that cleavage with β-secretase strictly depends on the amino acid sequence (Citron, M. et al., Neuron, 14, 661, 1995).

At present, for example, cathepsin B which is a cysteine protease (Tagawa, K. et al., Biochem. Biophys. Res. Commun., 177, 377, 1991) and metalloprotease having a molecular weight of 105 to 120 kDa (McDermott, J. R. et al., Biochem. Biophys. Res. Commun., 179, 1148, 1991) are reported to be candidates for α-secretase. Prolyl endopeptidase (Ishiura, S. et al., FEBS Lett., 260, 131, 1990) is reported to be a candidate for γ-secretase. Clipsin (Nelson, R. B. et al., J. Biol. Chem., 265, 3836, 1990) and ingensin (Ishiura, S. et al., FEBS Lett., 257, 388, 1989) are reported to be candidates for β-secretase.

Under these circumstances, it has been found neurosin as a novel serine protease which cleaves the N-terminus side of βAPP at between Met596 and Asp597 to produce Aβ. As described above, for conducting more detailed studies of Aβ and βAPP as well as Alzheimer's disease and Down's syndromes, a measuring system of neurosin is essentially required.

Nowadays, in general, clinical diagnosis of Alzheimer's disease is conducted based on the diagnosis standard of DSM-IIIR and NINCDS-ADRDA (Mckhann, G. et al., Neurology, 34. 939, 1994) or the diagnosis standard of DSM-IV (American Psychiatric Association; Diagnostic and statistical manuals of mental disorders, 4th ed., Washington D.C., American Psychiatric Association, 1994). However, these standards are conditioned by decline of recognition functions which causes a severe disability in a daily life or a social life. Then, it is pointed out that the diagnosis is less scientific objectivity because the diagnosis may be influenced by the level of an individual's social life and further the specialty and experience of a physician who diagnoses particular conditions. In addition, definite diagnosis of Alzheimer's disease is conducted by pathohistological analyses and, in this respect, substantial inconsistency between clinical diagnosis and autopsy diagnosis is pointed out.

At present, image diagnosis is employed as a supplemental means in clinical diagnosis of Alzheimer's diagnosis and it is possible to analyze brain functions, for example, decline of metabolism and atrophy in specific sites such as hippocampus, parietal lobe of cerebral cortex and the like which are specific for Alzheimer's disease by PET and SPECT (Fukuyama, H. et al., J. Nucl. Med., 35, 1, 1994). While it is difficult to analyze many cases by PET, there is a report showing that lowering of a blood flow from parietal lobe to temporal lobe is observed in about 80% of Alzheimer's disease cases based on SPECT data of blood flow observations in many cases (Haruo HANYUU, et al., Gazoshindan of Alzheimer's Disease, Nippon Ronen Igaku Zasshi, 31, 683, 1994). However, to define Alzheimer's disease based on lowering of a blood flow from parietal lobe to temporal lobe is very dangerous and it should be noted that, lowering of a blood flow in frontal lobe is found in some remaining cases. As to these observations, to differentiate Alzheimer's disease from degenerative cerebral atrophy such as Pick's disease and progressive aphasia as well as progressive supranuclear palsy is of importance, and only presently available reliable way is pathological diagnosis.

Further, while useful observations to be used for malignant tumor, angiopathy, diseases with metabolic change are obtained by MRS (Magnetic Resonance Spectroscopy) analyses, few reports are found with respect to patients with dementia including Alzheimer's disease. In particular, at present, a characteristic observation of dementia cannot be detected by 1H-MRS because of overlap with encephalatorophy observation such as the decrease in NAA (N-acetylaspartate) peak (Pettegrew, J. W. et al., J. Neuropathol., Exp., Neurol., 46, 419, 1987; Barany, M. et al., Lancet, i, 517, 1985; Smith, L. et al., Book of Abstracts, Society of Magnetic Resonance in Medicine 1986, Vol. 4, Berkeley, Society of Magnetic Resonance, 1386, 1986).

Furthermore, CT-MRI image diagnosis is used. By CT, one can observe localized atrophy weighted at temporal lobe and parietal lobe, and progressive generalized atrophy, as well as ventricular enlargement and periventricular low density (PVL) or change of white matter about ventricle called as leuko-araiosis in parallel with atrophy. However, white matter lesions such as atrophy of brain, PVL and the like are not specific characteristics of Alzheimer type dementia. Further, progress of atrophy of brain with aging is reported (Barron, S. A. et al., Neurology, 26, 1011, 1976; Zatz, L. M. et al., AJNR, 3, 1, 1982). Then, these observations are not necessarily found in Alzheimer type dementia.

MRI is very useful because, in particular, each site of brain can be observed at any imaging plane and can confirm presence of microangiopathy and the like which cannot be found out by X-ray CT. As to Alzheimer's disease, when imaging at an axial section and an arrowy section as well as a coronal section, observations which are overlooked by CT can be obtained. First, it has been found that atrophy of corpus callosum can be observed by imaging at an arrowy section from an early stage of the disease and it has been possible to conduct detailed observation of temporal lobe including hippocampus by imaging at coronal section. Further, in observation of brain parenchyma, cinerea can be readily differentiated from white matter by a proton weighted image. However, since an image obtained by MRI varies according to strength of a magnetic field, performance of an apparatus and imaging conditions, numerical data obtain in different facilities cannot be compared with each other except atrophic change. In addition, there is a limit to image measurement. Although area measurement is considered to be more sensitive than linear one and volume measurement is considered to be more sensitive than area measurement, it is difficult to conduct such measurement routinely. Further, enlargement of ventricle can be recognized in vascular dementia cases and there are cases wherein atrophy of hippocampus is observed after ischemia of basilar artery.

Under these circumstances, many researchers have requested to develop biological diagnosis markers as a means for providing better precision and objectivity for clinical diagnosis of Alzheimer's disease. At the same time, the following important roles in the future will be expected.

1) Objective judgment system of effect of medicaments for treating Alzheimer's disease.

2) Detection of Alzheimer's disease before a diagnosis standard is met, or disease conditions are manifested.

Further, data obtained in different facilities can be compared with each other by using the same diagnosis marker. Therefore, development of biological diagnosis markers is recognized to be a most important field among fields of Alzheimer's disease studies and its future prospects will be expected.

In general, approaches to development of biological diagnosis markers up to now are divided into that based on constitute components of characteristic pathological changes of Alzheimer's disease such as senile plaque and neurofibril change, and an approach based on other measures. Examples of the former include cerebrospinal fluid tau protein, Aβ and its precursor, βAPP. Examples of the latter include mydriasis test with cholilytic drug, Apo E and other genes relating to Alzheimer's disease. However, no good results are obtained.

The present inventors have expected that, from now, various brain diseases (e.g., Alzheimer's disease, Down's syndromes, etc.) can be identified by utilizing secretion of neurosin, whose expression is recognized in brain. in cerebrospinal fluid which is a useful sample for physiological studies of brain, and that secretion of neurosin can be used as an effective biological diagnosis marker even at an early stage of brain diseases . For this, a neurosin measurement system is also essential.

As described in WO98/11238, Protease M (i.e., neurosin) also plays an important role in cancer cells. The reason why extermination of cancer by surgical treatment or topical irradiation of radioactive ray is difficult is metastasis capability of cancer. For spread of solid tumor cells in a body, they should loosen their adhesion to original adjacent cells, followed by separating from an original tissue, passing through other tissues to reach blood vessel or lymph node, entering into the circulatory system through stratum basal and endothelial layer of the vessel, leave from the circulatory system at somewhere in the body, and surviving and proliferating in a new environment. While adhesion to adjacent epidermal cells is lost when expression of cadherin which is an intercellular adhesive molecule of epithelium is stopped, to break through tissues is considered to depend on proteolytic enzymes which decompose an extracellular matrix. As enzymes which decompose the matrix, mainly, metal proteases (Rha, S. Y. et al., Breast Cancer Research Treatment, 43, 175, 1997) and serine proteases are known. They cooperate to decompose matrix protein such as collagen, laminin and fibronectin. Among serine proteases known to be concerned in decomposition of the matrix, in particular, there is urokinase type plasminogen activator (U-PA) (Kinojo, M. et al., Br. J. Cancer, 39, 15, 1979; Danl, K. et al., Adv. Cancer Res., 44, 146, 1985; Nakanishi, K. et al., Cancer, 82, 724, 1998; Shiba, E. et al., J. Cancer Res. Clin. Oncology, 123, 555, 1997). U-PA has a role as a trigger specific for a protein decomposition chain reaction. Its direct target is plasminogen. It is present in blood abundantly and is a precursor of an inactive serine protease which accumulates in reconstructed sites of tissues such as injured sites and tumors as well as inflammatory sites. In addition, as proteases which are concerned in metastasis and infiltration of cancers, for example, a tissue factor (Kinjo, M. et al., Br. J. Cancer, 39, 15, 1979), lysosomal type hydrolase (Sloane, b. f. et al., Cancer Res., 42, 980, 1982) and collagenase (Mignatti, P. et al., Cell, 47, 487, 1986) have been known.

At present, cancer is the top cause of death in Japan and more than 200,000 people die per year. Then, specific substances which can be used as markers for diagnosis and therapy or prophylaxis of cancer is studied intensively. Such specific substances are referred to as tumor markers or tumor marker relating biomarkers. They are utilized in aid of diagnosis before treatment of cancer, for presuming carcinogenic organ and pathological tissue type, for monitoring effect of treatment, for finding recurrence early, for presuming prognosis, and the like. At present, tumor markers are essential in clinical analyses. Among them, alpha fetoprotein (AFP) which has high specificity to hepatocellular carcinoma and yolk sac tumor (Taketa K. et al., Tumour Biol., 9, 110, 1988), and carcinoembronic antigen (CEA) are used worldwide. In the future, tumor markers will be required more and more, and it is desired to develop, for example, organ specific markers and tumor cell specific markers which are highly reliable serologic diagnosis of cancer.

Up to now, human glandular kallikrein (hK2) which is a serine protease expressed at human prostatic epithelial cells has been reported as a marker for prostatic cancer. And, hK2 has 78% homology with the sequence of prostatic specific antigen (PSA) and PSA is also used widely as a biochemical marker of prostatic cancer (Mikolajczyk, S. d. et al., Prostate, 34, 44, 1998; Pannek, J. et al., Oncology, 11, 1273, 1997; Chu, T. M. et al., Tumour Biology, 18, 123, 1997; Hsieh, M. et al., Cancer Res., 57, 2651, 1997). Further, hK2 is reported to be useful as a marker for not only prostatic cancer but also stomach cancer (Cho, J. Y. et al.. Cancer, 79, 878, 1997).

Moreover, CYFRA (CYFRA 21-1) for measuring cytokeratin 19 fragment in serum is reported to be useful for lung cancer (Sugiyama, Y. et al., Japan J. Cancer Res., 85, 1178, 1994). Gastrin release peptide precursor (ProGRP) is reported to be useful as a tumor marker (Yamaguchi, K. et al., Japan, J. Cancer Res., 86, 698, 1995). Therefore, it is expected that combination of CYFRA and ProGRP may become a very useful means in aid of diagnosis for early diagnosis of lung cancer.

In particular, tumor markers are frequently used in diagnosis of ovarian cancer because, for example, ovarian cancer is difficult to find out at an early stage, is found out in its progressed state in many cases, has many varieties of tissue types, is difficult to presume the tissue type only by image diagnosis, is seldom benign ovarian tumor, and is required to differentiate from malignant one. At present, for example, CA125 which is a sugar chain relating antigen is used as a tumor marker of ovarian cancer clinically. However, it has been revealed that the average value of CA125 of a healthy person decreases with aging or after menopause. Then, it is required and desired to develop a marker which reinforces the weakness of CA125. In addition, for breast cancer, for example, CEA, TPA and CA15-3 are used. However, they are far from excellent markers in view of sensitivity and specificity and are insufficient for early diagnosis.

Under these circumstances, a serine protease, neurosin, which can be used as a marker for early breast cancer and early ovarian cancer has been found out. As described above, a measurement system of the serine protease, i.e., neurosin is essential for further detailed studies of metastasis and infiltration mechanism of cancer. In addition, from now, it is expected to be a biological diagnosis marker which can identify early ovarian cancer and early breast cancer, as well as can effectively diagnose them. For this, a neurosin measuring system is also desired.

Furthermore, although WO98/11238 describes a monoclonal antibody, in fact, no hybridoma is actually produced and no monoclonal antibody having specificity to a serine protease is actually obtained. Although this document discloses that the monoclonal antibody can be produced by known techniques, it is uncertain whether a hybridoma producing a monoclonal antibody specifically binding to a serine protease can be obtained in a screening step of hybridomas, or not.

OBJECTS OF THE INVENTION

In view of the above circumstances, the present inventors have undertaken the production of a monoclonal antibody specifically binding to a serine protease.

Thus, the main object of the present invention is to provide a monoclonal antibody specifically binding to neurosin which can be used for measuring the serine protease, neurosin.

This object as well as other objects and advantages of the present invention will become apparent to those skilled in the art from the following description with reference to the accompanying drawings.

BRIEF DESCRIPTION OF THE DRAWINGS

FIG. 5 illustrates comparison of the correlation between western blotting and an ELISA system of patient's specimens (electrophoretic photograph).

FIG. 7 illustrates the results of N-terminus amino acid sequencing of neurosin derived from human CSF.

FIGS. 9A and 9B are those obtained by using neurologically normal brain tissues. FIGS. 9C–9F are those obtained by using brain tissues of patients with Alzheimer's disease.

FIG. 9A: The nuclei of nerve cells present in parietal lobe cinerea and having axons were stained similar to other cells.

FIG. 9B: The nuclei of glia cells were stained in parietal lobe white matter.

FIGS. 9C and 9D: Only a few nerve cells present in parietal lobe and having axons were stained in case of brain with Alzheimer's disease. The nuclei and nucleoli of the nerve cells were stains (shown by arrow head). Senile plaque was also stained with anti-neurosin antibody (shown by arrow).

FIG. 9E: Cone cells present in CA4 region of hippocampus and having axons were neurosin positive cells.

FIG. 9F: Extracellular neurofibril change region present in CA1 region of hippocampus was neruosin positive.

FIGS. 10A and 10B are those obtained by using neurologically normal brain tissues.

FIGS. 10C and 10D are those obtained by using midbrain tissues of patients with Parkinson's disease.

FIG. 10A: Many nerve cells present in oculomotor nerve were neurosin positive similar to glia cells.

FIG. 10B: Some of melanin-containing cells were neurosin positive.

FIG. 10C: In brain with Parkinson's disease, the number of melanin-containing became very few and a small number of remaining nerve cells were neurosin positive.

SUMMARY OF THE INVENTION

Figure 1:
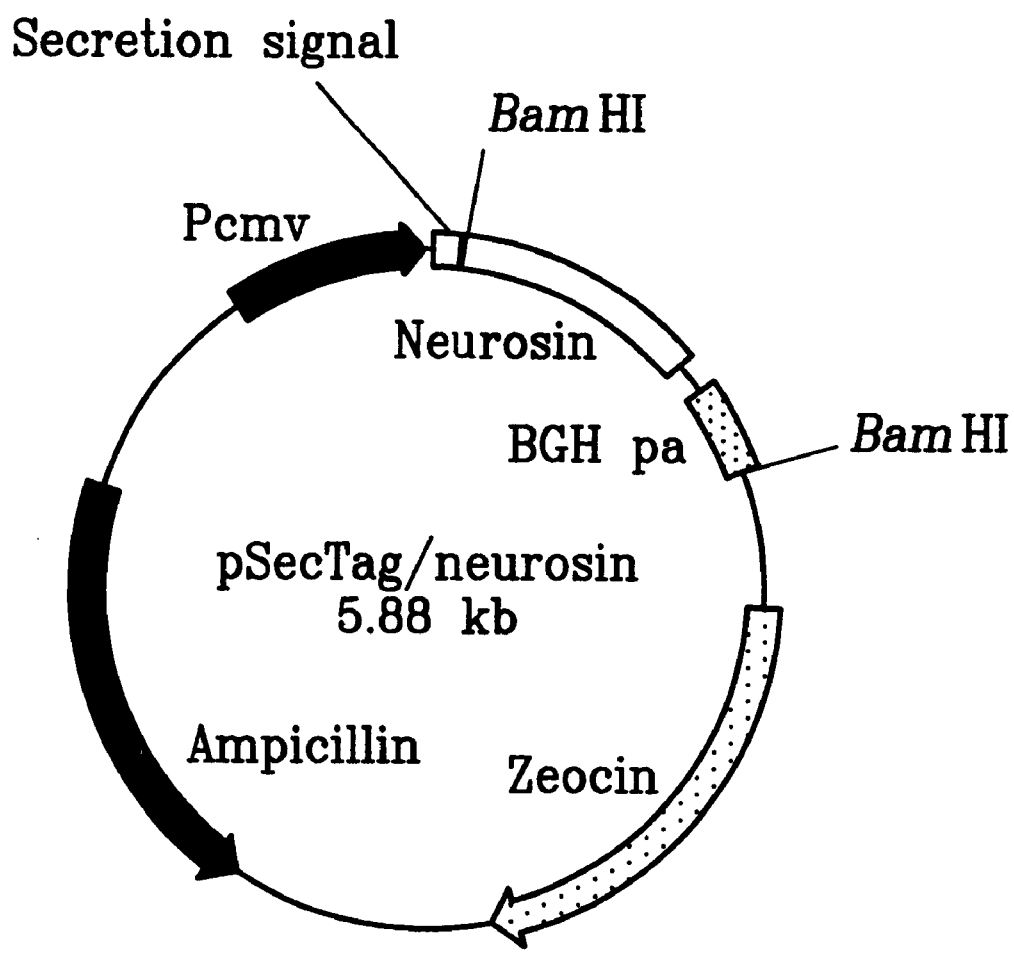
FIG. 1 is a gene map of expression plasmid pSecTag/neurosin.

The present inventors have studied intensively to provide a method for determination of neurosin having excellent specificity and good sensitivity. As a result, it has been found that a monoclonal antibody having excellent specificity can be obtained by using recombinant neurosin as an antigen. Thus, the present invention has been completed. The present invention provides at least one monoclonal antibody which can be used for determination of neurosin in a specimen.

Further, the present invention provides a pharmaceutical composition for diagnosing Alzheimer's disease and a diagnosis method of the same using the monoclonal. The present invention also provides a pharmaceutical composition for diagnosing Parkinson's disease and a diagnosis method of the same.

DETAILED DESCRIPTION OF THE INVENTION

According to the present invention, monoclonal antibodies against neurosin and two kinds of hybridomas producing the antibodies, 2B2-6 cell strain and S2E5 cell strain have been obtained. These hybridomas have been deposited at National Institute of Bioscience and Human-Technology (NIBH), Agency of Industrial Science & Technology of 1-1-3 Higashi, Tsukuba-shi, Ibaraki-ken, Japan, now under the accession numbers of FERM P-7341 and FERM P-7342, respectively, since Jun. 17, 1998. Both monoclonal antibodies produced by these hybridomas 2B2-6 cell strain and S2E5 cell strain have the isotype of IgG1 for H chain IgG1 and κ for L chain. The present invention includes class switching mutants of the above antibodies, for example, mutants belonging to isotype IgG3, IgG1, IgG2b, IgG2a and other immunoglobulin subclasses, and such mutants can be produced according to the method of Marin et al. (Coco, Martin et al., J. Immunol. Methods, 145, 1118, 1991).

For production of an antibody against neurosin, neurosin to be used as an immunogenic antigen is required. Naturally derived neurosin as an antigen can be more highly purified by subjecting to, for example, affinity chromatography using a polyclonal antibody. In addition to naturally derived one, preferably, neurosin can be obtained by cultured cells, for example, neurosin producing cells. Examples of neurosin producing cells include cells derived from human brain, cells derived from human salivary glands, cells derived from human kidney, cancer cells and the like. These neurosin producing cells can be cultured by a culture medium and a culture method known in this art field or the substantially same ones. The neurosin produced in a culture supernatant can be purified by, for example, ion exchange chromatography and/or affinity chromatography using a polyclonal antibody.

In addition, recombinant neurosin can be used. Specifically, host cells are transformed by a recombinant vector containing a gene fragment having a nucleotide sequence encoding the amino acid sequence of neurosin, followed by culturing the resultant transformant to produce a polypeptide containing the amino acid sequence of neurosin and using it as an antigen. A recombinant vector containing cDNA of neurosin can be constructed by conventional gene recombinant techniques, for example, insertion into a plasmid vector. Examples of the vector to be used include viruses such as vaccinia virus, baculovirus and the like in addition to plasmids and phages.

Examples of the host to be used include procaryote such as E. coli, Bacillus subtilis and actinomycetes, as well as eucaryote such as various cells, for example, animal cells and commercially available cell strains, e.g., CHO cells, and further, plant cells and insect cells. Examples of the promoter to be used for procaryote include tryptophan synthase operon, lactose operon and the like. Examples of the promoter to be used for eucaryote include virus promoter, promoter for alcohol dehydrogenase, promoter for glycolytic pathway enzyme and the like. In addition, commercially available vectors and plasmids having multicloning site, promoter, resistant gene, ori, terminator, ribosome binding site and the like can also be used. The resistant gene includes that against tetracycline, ampicillin, neomycin or the like. The neurosin thus prepared can be further converted into an antigenic conjugate, or can be used as it is for immunizing an animal by mixing it with a suitable adjuvant.

Thus, the antigen can be obtained from various starting materials, for example, antigen producing raw materials such as cultured cells, cultured tissue and transformant cells by purifying according to a known method, for example, salting out such as ammonium sulfate precipitation, gel filtration with Sephadex or the like, ion exchange chromatography, hydrophobic chromatography, pigment gel chromatography, electrophoresis, dialysis, ultrafiltration, affinity chromatography, or high performance liquid chromatography.

Further, neurosin may be a fragmented product thereof, or a polypeptide fragment obtained by cloning and determining a cDNA sequence of neurosin, deducing the amino acid sequence, selecting a characteristic sequence region based on the amino acid sequence to design a polypeptide and then synthesizing the designed polypeptide chemically. The fragment can be attached to various carrier proteins through a condensing agent to form hapten-protein immunoconjugates. This can be used for designing a monoclonal antibody which can recognize only a specific sequence. For facilitating preparation of an immunogenic conjugate, cysteine residue or the like can be added to a polypeptide to be designed beforehand.

According to the present invention, there is provided at least one monoclonal antibody which binds specifically to neurosin. The monoclonal antibody of the present invention can be produced by steps such as immunization of animal with recombinant neurosin as an immunogen, followed by cell fusion of myeloma cells and antibody producing cells, selection and monocloning of a hybridoma, production of the monoclonal antibody and, if necessary, collection of ascites. It is necessary to prepare myeloma cells before cell fusion. A tumor cell strain to be used before cell fusion can be selected from those not producing immunoglobulin.

Example of an adjuvant to be used together with the antigen include Freund's complete adjuvant, RIBI adjuvant, pertussis adjuvant, BCG, liposome, aluminum hydroxide, silica gel and the like. For immunization of an animal, for example, mice such as Balb/c mouse, F1 mouse and the like can be used. On the other hand, according to the present invention, it is possible to produce a polyclonal antibody against neurosin by using recombinant neurosin. The antibody may be an antiserum. It may be a further purified antibody.

Cell fusion of antibody producing cells and myeloma cells can be carried out as follows. The spleen cells or lymph node cells of an immunized animal is removed to obtain a cell suspension. The resultant cell suspension and myeloma cells are placed in MEM, DMEM or RPMI-1640 culture medium and a fusion promoting agent such as polyethylene glycol or the like is added thereto. If necessary, a small amount of dimethylsulfoxide is added to further promote cell fusion.

The hybridomas thus obtained can be selected by using a culture medium such as MEM culture medium or RPMI-1640 culture medium containing hypoxanthine, aminopterin and thymidine and further FCS. Culture supernatants of the hybridomas are subjected to screening by, for example, radioimmunoassay, ELISA, FIA or flow cytometry using neurosin or its fragment peptide as an antigen, or labeled anti-mouse antibody to separate the desired hybridoma.

The hybridoma thus cloned is cultured and used for producing the monoclonal antibody. The hybridoma can be cultured in a suitable culture medium such as MEM culture medium or RPMI-1640 culture medium containing FCS, and the desired monoclonal antibody can be obtained from the culture supernatant. For obtaining a large amount of the monoclonal antibody, the hybridoma can be collected in ascites. In this case, each hybridoma can be transplanted intraperitoneally in an animal having histocompatibility with the animal from which the myeloma cells are derived and proliferated therein, or each hybridoma can be implanted in a nude mouse or the like, followed by collecting the monoclonal antibody produced in the ascites. Pristane or the like is administered to the animal intraperitoneally before transplantation of the hybridoma. The ascites fluid can be used as it is, or it can be purified by a conventional method. For example, it can be purified by salting out such as ammonium sulfate precipitation, gel filtration with Sephadex or the like, ion exchange chromatography, electrophoresis, dialysis, ultrafiltration, affinity chromatography, or high performance liquid chromatography.

Examples of a substance to be used for labeling the antibody include enzyme, enzyme substrate, coenzyme, enzyme precursor, apoenzyme, fluorescent substance, pigment substance, chemical luminescent compound, luminous substance, color producing substance, magnetic substance, metal particle, radioactive substance and the like. For labeling the antibody, for example, the reaction of thiol group with maleimide group, that of pyridylsufide group with thiol group, or that of amino group with aldehyde group can be utilized.

As embodiments of the present invention, the antibody of the present invention can be used in immunostaining, for example, staining of tissue or cells immunologically, immunoprecipitation, immunoblotting, immunoassay, for example, competitive or non-competitive immunoassay, radioimmunoassay, ELISA, latex agglutination, protein purification, affinity column and the like. In case of ELISA, a sandwich type assay is preferred. The immunoassay includes all methods such as immunohistological studies, immunoblotting, and methods utilizing immunological reactions, for example, immunoprecipiation and the like.

Specimens and samples to which the monoclonal antibody of the present invention can be applied may be in any form including solutions, colloidal fluids and non-fluid samples. Preferably, they are samples derived from living bodies such as blood, serum, joint fluid, cerebrospinal fluid, saliva, amniotic fluid, urine, other body fluids, cell culture fluid, tissue culture fluid, tissue homogenate, biopsy sample, cells, tissue, brain tissue, cell line derived from brain, nerve cell line, cell line derived from nerve, cell line derived from milk line, milk line tissue, cell line derived from ovary, ovarian tissue, cancer cells, cancer tissue and the like.

Accordingly, the present invention also provide such hybridoma cell strain, an immunoassay and an assay kit.

Further, the present invention provides the monoclonal antibody which recognizes neurosin specifically, an immunoassay for detecting and quantitative determination of neurosin characterized by using this antibody and an assay kit for conducting this immunoassay.

In addition, as seen from Example 4 hereinafter, the monoclonal antibody obtained by the present invention shows no cross reactivity with IgG, albumin and trypsinogen and has high specificity to neurosin. Then, it is very useful for detection and quantitative determination of neurosin.

Further, as seen from Example 5 hereinafter, the monoclonal antibody of the present invention has immunoreactivity with not only mature type neurosin but also its pro-form. In general, after translation, proteins undergo various kinds of processing to produce active type proteins. First, many secretory proteins are synthesized on ribosomes in a cell in the form of inactive precursor type proteins (pro-form). Such inactive pro-form has a peptide (secretion signal) which is concerned in secretion and is composed of, normally, about 15 to 60 amino acid residues at the N-terminus of the corresponding active type protein. This peptide part relates to a mechanism for passage of the protein through the cell membrane and, in almost all cases, it is cleaved and removed by a specific enzyme upon passing through the membrane to form the corresponding mature type protein. A secretion signal has a broad hydrophobic region composed of hydrophobic amino acids in the center thereof and also has a basic amino acid residue at a site closed to its N-terminus. Further, there is a certain protein which has an additional secretion signal at the N-terminus of an inactive precursor type protein (pro-form) and such a protein is referred to as a preproprotein (prepro-form).

For example, trypsin exists in the prepro-form immediately after translation into amino acids and, after secretion from the cell, it exists in the pro-form. Then, it undergoes limited decomposition with enteropeptidase or trypsin itself in duodenum to convert into active type trypsin.

The term "pro part" used herein means the part of a pro-form from which the corresponding active type protein part is removed. The term "pre part" used herein means the part of a prepro-form from which the corresponding pro-form is removed. The term "prepro part" used herein means the part of a prepro-form from which the corresponding active type protein part is removed.

Without exception, neurosin is also translated in the prepro-form. Then, it is converted into its pro-form and the pro part is removed to form active neurosin.

As described above, it has been found that the monoclonal antibody of the present invention has immunoreactivity with not only mature type neurosin but also its pro-form. That is, it has been found that neruosin present in cerebrospinal fluid is in the pro-form and that the monoclonal antibody obtained by the present invention has immunoreactivity with not only recombinant active neurosin but also naturally occurring neurosin.

The monoclonal antibody of the present invention can be used for diagnosis of Alzheimer's disease and Parkinson's disease.

There is a report that serine proteases in brain are concerned in a development stage, synaptic plasticity and neurological diseases including Alzheimer's disease. Recently, Davies et al. have reported that tissue plasminogen activator (RNK-Met-1) as well as BSP1 and BSP2 which are brain serine proteases are highly expressed from rat brain hippocampus (Davis, B. J. et al., J. Biol. Chem., 273, 23004–23011, 1998). BSP1 and BSP2 are novel trypsin-like proteases and BSP1 has been defined as neuropsin (Chen, Z. -L. et al., J. Neurosci., 15, 5083–5097, 1995).

Recently, novel trypsin-like serine protease highly expressed in brain has been cloned and defined as neurosin (Yamashiro, K. et al., Biochem. Biophys. Acta, 1350, 11–14, 1997). Neurosin is composed of 244 amino acids and is similar to serine protease family. Further, neurosin has 28.4% homology to human trypsinogen 1, 26.3% homology to human trypsinogen 2, 22.9% homology to human kallikrein, 13.8% homology to human factor X and 12.5% homology to human chymotrypsinogen. However, it does not cleave substrates for thrombin, chymotrypsin and plasmin. In view of this, neurosin is considered to play a trypsin-like role in brain.

Further, as shown in Examples 6 and 7 hereinafter, as a result of immunostaining of a brain tissue slice with the monoclonal antibody of the present invention, all the nuclei present in brain were stained. In addition, as to nerve cells, their nerve cytoplasm, nerve cell nuclei and axons were stained. To the contrary, axons present in a disorder site of brain of a patient with Alzheimer' disease were scarcely stained. Presence of neurosin was confirmed in senile plaque, extracellular neurofibril change region and Lewy bodies. In view of this, neurosin considered to be concerned in decomposition of protein such as β-amyloid.

Furthermore, according to the present invention, it has been shown that neurosin is present in various kinds of cells in brain.

In contrast to glia cells wherein neurosin is specifically present in their nuclei, as to nerve cells, cytoplasm, nuclei, nucleoli and their axons are neurosin positive. Neurosin is scarcely contained in nerve cells of a disorder site of a patient with Parkinson's disease or Alzheimer's disease. In brain with Alzheimer's disease, neurosin is present in several senile plaques and neurofibril change region.

Amyloid precursor protein (APP) are divided into three types (APP695, APP751 and APP770) according to the number of amino acids. APP751 and APP770 contain 56 amino acids having functions of Kunitz-type serine protease inhibitor (KPI). Recently, Moir et al. have reported that brain of a patient with Alzheimer's disease has a significantly higher ratio of APP species including KPI in comparison with normal brain (Moir, R. d. et al., J. Boiol. Chem., 273, 5013–5019, 1988). They have suggested that, in later Alzheimer's disease, an increase in these amyloid producing products are concerned in amyloid precipitation.

The secreted isoform containing KPI domain is the same as protease nexin 2 (PN-2). PN-2 is known to be an inhibitor of serine proteases such as trypsin (Kitaguchi, N. et al., Nature, 331, 530–532, 1988; Sinha, S. et al., J. Biol. Chem., 265, 8983–8985, 1990), Chymotrypsin (Kitaguchi, N. et al., Nature, 331, 530–532, 1988, Sinha, S. et al., J. Biol. Chem., 265, 8983–8985, 1990), Factor IXa (Schmaier, A. H. et al., J. Clin. Invest., 92, 2540–2543, 1993), Xa (Mahdi, F. et al., J. Biol. Chem., 270, 23468–23474, 1995) and XIa (Van Nostrand, W. E. et al., J. Biol. Chem., 265, 9591–9594, 1990). There are reports showing that trypsin (Smith, M. a. et al., Mol. Chem. Neuropathol., 27, 145–154, 1996; Wiegan, U. et al., Gene, 136, 167–175, 1993), Factor Xa (Hass, C. et al., Bioch. Biophys. Acta, 1343, 85–94, 1997), XIa (Saportito-Irwin, S. M. et al., J. Biol. Chem., 270, 26265–26269, 1995), other serine proteases and thrombin (Igarashi, K. et al., Biochem. Biophysic. Res. Com., 185, 1000–1004, 1992), and novel chymotrypsin-like enzyme (Little, S. P. et al., J. Biol., Chem., 272, 25135–25142, 1998) are enzymes concerned in processing of APP. Further, thrombin (Akiyama, H. et al., Neurosci. Lett., 146, 142–154, 1992) and trypsin (Smith, M. A. et al., Mol. Chem. Neuropathol., 27, 145–154, 1996) are shown to be localized in β-amyloid precipitated site of brain with Alzheimer's disease.

The present inventors have shown that neurosin is an enzyme concerned in amyloid precipitation because it is localized in senile plaque. Further, there is a report that APP binds to a membrane and is cleaved with a secretase (Roberts, S. B. et al., J. Biol. Chem., 269, 3111–3116, 1994; Vassilacopoulou, D. et al., J. Neurochem., 64, 2140–2146, 1995). Neurosin is considered to be concerned in processing of APP because it is also present in a membrane fraction. Neurosin is considered to be secreted from nerves and to play a certain role in proteolysis of pathogenic tissue structure because extracellular neurofibril change is stained by the anti-neurosin antibody. Trypsin has already been reported to be present in a neurofibril change region (Smith, M. A. et al., Mol. Chem. Neuropathol., 27, 145–154, 1996). There is a possibility that neurosin has proteolytic function of aggregate structure because it is present in Lewy bodies.

That is, neurosin is considered to be concerned in Alzheimer' disease and Parkinson's disease and, therefore, it is possible to diagnose a diseases in which neurosin is concerned by detecting and determining the expressed amount of neurosin.

In addition, while Examples 6 and 7 hereinafter are experimental systems using the monoclonal antibody against neurosin, the same effect as that of these experimental systems can be expected by using an experimental system which is targeting on mRNA of neurosin. Then, the above diseases can also be diagnosed by using mRNA obtained from a sample or specimen.

Further, since two monoclonal antibodies obtained in the present invention have different specificity to neurosin, further improved specificity can be obtained by combining them, and therefore diagnosis of the above diseases can be conducted with high sensitivity.

Moreover, when the monoclonal antibody of the present invention is administered to a human being for diagnosis or treatment of a neurosin-related disease, a method for minimizing antigenecity against the human being can be employed. That is, this can be conducted by converting the monoclonal antibody of the present invention into a chimera antibody or a humanized antibody according to a known method. The monoclonal antibody of the present invention includes these antibodies which decrease their antigenecity against a human being. Hereinafter, a method for producing the antibody will be illustrated.

The term "chimera antibody" means a chimera molecule of a mouse antibody and a human antibody. It is impossible to produce an antibody by immunizing a human being with any antigen from the ethical viewpoint. Then, a mouse is immunized and an antibody variable region (V region) which binds to an antigen is cut out from a gene of a mouse monoclonal antibody, followed by joining it to an antibody constant region (C region) gene derived from a human bone tumor to produce a chimera gene. A human-mouse monoclonal antibody can be produced by expressing the chimera gene in a host cell. Since the chimera antibody has less antigenecity against a human being, it can be used as the monoclonal antibody for administering to a human being to treat a disease or to conduct image diagnosis. As techniques relating to known chimera antibodies, there are those described in JP 5-304989 A, JP 4-33-295, WO91/06649, JP 63-036786 A, JP 6-98021 and the like.

However, recently, a humanized antibody which is more useful than a chimera antibody has been developed. A humanized antibody is obtained by transplanting only a gene sequence of an antigen-binding site (CDR: complementary determining region) in an antibody molecule into a human antibody gene (CDR grafting) to humanize the whole molecule except CDR of the antibody molecule. Since a mouse antibody part in this antibody is less than that in a human-mouse chimera antibody, this antibody is said to have less antigenecity and higher safety than the human-mouse chimera antibody. In Japan, at present, a clinical test of a humanized antibody against adult T cell leukemia is conducted. Patent applications directed to the production processes of humanized antibodies and related techniques have been filed by a U.S. company, Genentech (WO92/22653, WO98/45332, WO94/04679, WO98/37200, WO94/04679), a U. K. company, Celltech (WO94/29451, WO94/29351, WO94/13805, WO93/06231, WO92/01059, WO91/16927, WO91/16928, WO91/09967, WO89/01974, WO89/01783), and the like.

There is danger in administration of a mouse monoclonal antibody because the antibody is a foreign protein for a human being and is liable to cause side effects. Then, a human monoclonal antibody is desirable. However, heretofore, fusion efficiency was insufficient and it was difficult to obtain a hybridoma stably producing an antibody. Nevertheless, at present, an advance in technology makes it possible to produce a human monoclonal antibody.

As a production process of a human monoclonal antibody, in addition to a cell fusion technique, there are, for example, transformation with Epstein-Barr virus (EBV), fusion of cells obtained transformed with said virus with parent cells, and a method for producing a chimera antibody and a humanized antibody by utilizing genetic engineering. An chimera antibody is an antibody obtained by joining immunoglobulin gene fragments of animals of different species to each other. A humanized antibody is an antibody obtained by modifying an antibody heterogeneous to a human being such as a mouse antibody to replace its primary structure other than CDR of H chain and L chain with the corresponding primary structure of a human antibody. When SHM-D 33 strain (ATCC CRL 1668) or RF-S1 strain which is a heteromyeloma of human being/mouse is used as parent cells for producing a human monoclonal antibody, the same high fusion efficiency as that using parent cells of mouse can be obtained. A hybridoma obtained by using these parent cells can be cloned without feeder cells. Then, an IgG type antibody can be produced relatively stably in a large amount. For culturing the parent cells, ERDF culture medium supplemented with 15% FCE is used and the other procedure is the same as that of mouse. In addition, for producing a IgG type human monoclonal antibody, it is preferred to use human lymphocytes collected from peripheral blood which is sufficiently sensitized with an antigen. When lymphocytes sensitized sufficiently with an antigen is hardly available, sensitization with an antigen can be conducted in vitro.

By using the above method, the antibody of the present invention can be humanized and it is very useful for administration to a human being.

The following Examples further illustrate the present invention in detail but are not construed to limit the scope thereof.

EXAMPLE 1

Production of anti-neurosin monoclonal antibody

An anti-neurosin monoclonal antibody was produced according to the following procedure.

(a) Preparation of Antigen (Production of Cells Expressing Recombinant Neurosin Protein)

According to the same manner as that described in JP 9-14790 A or Biochim. Biophys. Acta,1350, 11, 1997, mRNA was prepared from COLO201 cells, followed by synthesizing cDNA and cloning pSPORT/neurosin.

A translation region of the mature protein was obtained from pSPORT/neurosin by PCR and this was introduced into pSecTagB (manufactured by Invitorgen) to construct an expression plasmid. First, sequences recognized by the restriction enzyme BamHI were added to 5' and 3' termini of the translation region of neurosin to prepare primers. They are shown by SEQ ID NOS: 1 and 2.

```
SEQ ID NO: 1:    CGCGGATCCTTGGTGCATGGCGGACCC

SEQ IN NO: 2:    CGCGGATCCTCACTTGGCCTGAATGGT
```

PCR amplification was carried out by using these primers and pSPORT/neurosin as a template to obtain a BamHI recognizing sequence added neurosin translated region. This PCR product and pSecTagB were digested with the restriction enzyme BamHI and ligated by using a ligation kit Ver. 1 (manufactured by Takara) to transform into *E. coli* JM109 (manufactured by Takara). Among transformed colonies, a colony containing neurosin gene was confirmed by PCR to obtain an expression plasmid pSecTag/neurosin. Its gene map is shown in FIG. 1.

A recombinant neurosin protein was produced by using the expressed plasmid pSecTag/neurosin and CHO cells. CHO cells ($1\times10^6$ cells) were seeded in a culture dish of 10 cm diameter (manufactured by Corning). On the following day, the cells were rinsed with Opti-MEM™ (Minimal Essential Medium, 5 ml) (manufactured by GIBCO), followed by addition of fresh Opti-MEM™ (5 ml) and culture at 37° C. for 2 hours. Then, pSecTag/neurosin (1 µg) and Lipofectamine™ (manufactured by GIBCO BRL) (10 µl) were added to the cells and the cells was cultured at 37° C. for 6 hours. After the transfection, the cells were washed with 10% fetal bovine serum-added α-MEM and cultured in a 25 cm² T-shaped flask. After introduction of the gene, Zeosin™ (manufactured by Invitrogen) was added to the medium and only cells into which the plasmid had been introduced were selected by drug selection. The medium was exchanged twice in a week and the culture was continued until cells became confluent. Cells thus cultured until they became confluent were released from the flask and subcultured.

The neurosin expressing cells thus obtained were cultured in a serum-free medium and recombinant neurosin was obtained from the culture supernatant. Then, the culture supernatant was centrifuged at 1,5000 r.p.m. for 15 minutes, dialyzed by using a MES buffer (Dozin), and passed through two cation exchange resins (Hitrap-SP™ and Mono-S™ manufactured by Pharmacia) equilibrated with the same buffer. Next, it was purified by passing through a gel filtration column (Sephacril S-200™ manufactured by Pharmacia) with PBS (Phosphate Buffered Saline) to obtain an antigen solution.

For example, in case of using another vector having no secretion signal, cells are precipitated with PBS containing Triton-X 100™ or Tween-20™ and the precipitated cells are disrupted to obtain recombinant neurosin. Alternatively, cells are disrupted mechanically with, for example, a homogenizer or a sonicator to obtain recombinant neurosin. A supernatant of a soluble fraction which is purified by the above method after centrifugation of disrupted cells can also be used.

In addition, an expression plasmid, pdKCR/Trp59, is constructed according to the method described in JP 9-14790 A or Biochim. Biophys. Acta, 1350, 11, 1997 and CHO cells are transformed by introduction of the plasmid therein. The transformed CHO cells are cultured according to the above-described method and recombinant neurosin is purified from the culture supernatant. This can also be used as an antigen solution.

Further, naturally occurring human neurosin can be purified from a culture supernatant (10 L) of a high producing protein-free cultured cell strain of natural neurosin, HPC-Y3, by gel filtration, ion exchange column, hydrophobic chromatography, preparative acrylamide electrophoresis and the like. This can also be used as an immunogen.

(b) Immunization

The antigen solution for immunization prepared in the above (a) was mixed with Freund's complete adjuvant (manufactured by DIFCO) in the ratio of 1:1 and the mixture was emulsified. The emulsion was injected into five female Balb/C mice (8-week old, about 100 µg/mouse of neurosin protein) subcutaneously. Then, booster immunization (about 100 µg/mouse of neurosin protein) was conducted three times at about 2 week intervals by subcutaneous injection of an emulsified mixture of the antigen solution for immunization and Freund's incomplete adjuvant (manufactured by DIFCO) in the ratio of 1:1. Three days after the third booster, a blood sample was collected from the tail vein and the antibody titer in the serum was measured by the ELISA hereinafter. Two weeks after the third booster, a solution of the antigen solution for immunization in physiological saline (about 100 µg/mouse of neurosin protein) was administered to the mice intraperitoneally. Three days after the administration, spleen cells were prepared from the immunized mice for using them in the cell fusion hereinafter.

(c) ELISA (Direct Solid Phase Method)

A neurosin protein solution prepared by the same manner as that in the preparation of the immunization antigen was adjusted to 5 µg/ml with PBS and the solution (50 µl/well) was adsorbed by a ELISA plate for 2 hours. The plate was blocked by a 4-fold dilution of Blockace™ (manufactured by Snow Brand Milk Products) in PBS. After washing the plate, a 5,000-fold dilution (50 µl/well) of the serum obtained in the above (b) in a serum diluting buffer (PBS containing 5% FBS) was added to each well of the plate and reacted at room temperature for 2 hours. After washing the plate, a 2,000-fold dilution (50 µl/well) of alkaline phosphatase labeled mouse IgG antibody (manufactured by ICN/Cappel) was added to each well of the plate and reacted at room temperature for 1 hour. Disodium p-nitrophenyl phosphate (SIGMA 104 phosphatase substrate tables) was dissolved in a substrate reaction mixture (9.6% diethanolamine buffer containing 0.5 mM magnesium chloride, pH 9.7) at concentration of 2 mg/ml to prepare a substrate solution. The plate was washed 7 times with purified water and the substrate solution (50 µl/well) was added thereto. After reaction with the substrate solution, 3N NaOH (50 µl) was added to stop the reaction and the absorbance at 405 nm was measured.

(d) Cell Fusion and Production of Hybridoma

Three days after the last immunization, the spleens were excised from three mice which showed an increase in the antibody titer against neurosin protein as the results of the above ELISA and, according to a conventional method, spleen cells were prepared. The parent cells to be fused were Balb/c mouse-derived myeloma SP cell strain which was confirmed to be a hypoxanthine-guanine phosphoribosyl transferase (HGPRT) defect strain beforehand by selection with a culture medium containing 8-azaguanine (20 µg/ml). SP2 cells ($2\times10^7$ cells) and spleen cells ($1\times10^8$ cells) were combined and cell fusion was conducted according to a conventional manner by using polyethylene glycol 4000 (PEG4000™, manufactured by Merck) as a cell fusion promoter. After completion of cell fusion, the cells were suspended in a culture medium (HAT medium) prepared by adding hypoxanthine, aminopterin and thymidine to Esclone™ medium (manufactured by Sanko Pure Chemicals) in concentration of $3.0\times10^8$ cells/ml in terms of the spleen cells, and distributed into a 96-well microplate (manufactured by Corning) (100 µl/well). The fused cells were cultured in a $CO_2$ incubator (37° C., 5% $CO_2$) with exchanging a half of the medium every 3 to 5 days. Only hybridomas which survived in the medium were selected and cultured.

(e) Screening of Hybridoma

Regarding the wells whose colony formation were confirmed, screening was carried out by the same ELISA as that of the above (c) to confirm the presence of an antibody against neurosin protein in the culture supernatant. Two kinds of plates to which neruosin and trypsinogen were adsorbed, respectively, were used and colonies which strongly reacted with neurosin protein were selected and cloned.

(f) Screening of Hybridoma

Cloning of hybridomas which produced antibodies binding to neurosin protein was repeated three times by limited dilution to obtain two kinds of hybridomas, 2B2-6 cell strain and S2E5 cell strain which produced antibodies specifically binding to neurosin protein and had stable proliferation capability. These hybridomas were deposited at National Institute of Bioscience and Human-Technology (NIBH), Agency of Industrial Science & Technology of 1-1-3 Higashi, Tsukuba-shi, Ibaraki-ken, Japan on Jun. 17, 1998 and now have the accession numbers of FERM P-7341 and FERM P-7342, respectively.

(g) Typing of Monoclonal Antibody

The isotype was examined by using culture supernatants (each 0.5 ml) of the above-obtained two hybridomas, 2B2-6 cell strain and S2E5 cell strain with Mouse Antibody Isotyping Kit™ (manufactured by Gibco BRL). Both isotypes of monoclonal antibodies produced by the hybridomas 2B2-6 cell strain and S2E5 strain were the same. Namely, H chain was IgG1 and L chain was κ.

(h) Preparation and Purification of Monoclonal Antibody

Pristan (0.5 ml/mouse) was administered to female Balb/c mice (8-week old) intraperitoneally and, ten days after administration, two hybridomas 2B2-6 cell strain and S2E5 cell strain obtained in the above cloning (d) (about $10^7$ cells/0.5 ml/mouse, respectively) were injected intraperitoneally. Since about 10 days, abdominal hypertrophy of mice was observed. Then, ascites was collected by a 18G injection needle. The ascites collected was centrifuged at 1,000 r.p.m. at 4° C. for 10 minutes and the supernatant was allowed to stand at 37° C. for 30 minutes. Further, it was allowed to stand at 4° C. overnight. After centrifugation at 12,000 r.p.m. at 4° C. for 10 minutes, the resultant supernatant was subjected to an affinity column with Sephrose Protein A™ (manufactured by Pharmacia Bioteck) to purify the respective monoclonal antibody. The absorbance of a solution of the antibody was measured at 260, 280 and 320 nm and the antibody concentration was determined by Werbulg-Christian method.

(i) Western Blotting

Expression of recombinant neurosin protein was confirmed as follows.

After recovery of the culture supernatant of respective cloned cells, it was mixed with an equal amount of 2×SDS loading buffer (manufactured by Daiichi Kagaku) and the mixture was heated in a boiling bath for 5 minutes. This was used as a sample solution. The sample solution was subjected to electrophoresis on 10 to 20% polyacrylamide gel (manufactured by Daiichi Kagaku) by using a SDS electrophoresis apparatus (manufactured by Daiichi Kagaku) and Tris-glycine buffer (manufactured by Daiichi Kagaku). On the other hand, for blotting, two sheets of 3MM filter paper (manufactured by Whattman) were dipped in Buffer A (manufactured by Daiichi Kagaku), one sheet of the filter paper was dipped in Buffer B (manufactured by Daiichi Kagaku) and three sheets of the filter paper were dipped in Buffer C (manufactured by Daiichi Kagaku) during the electrophoresis. Further, a polyvinylidene fluroide membrane (PVDF membrane, manufactured by Milipore) was dipped in methanol and then in water to adapt it to water.

Transcription of the protein to the PVDF membrane was carried out by taking out the gel from the apparatus after electrophoresis, and placing 2 sheets of the filter paper dipped in Buffer A, one sheet of the filter paper dipped in Buffer B, PVDF membrane, the gel and 3 sheets of the filter paper dipped in Buffer C in a blotter (manufactured by Pharmacia) from its cathode side in this order and applying a voltage of 8 mV for 1.5 hours. After transcription, PVDF membrane was blocked by shaking it together with Blockace™ (manufactured by Snow Brand Milk Products) at room temperature for 1 hour. The membrane was reacted with a dilution of rabbit anti-neurosin polyclonal antibody prepared in Example 2 hereinafter with 5% fetal bovine serum added PBS at 4° C. for overnight. After 3 times of washing the membrane with PBS containing 0.05% Tween 20™ (PBS-T) for 5 minutes, alkaline phosphatase labeled anti-rabbit IgG antibody was added thereto and, after reaction at room temperature for 1 hour, followed by 3 times of washing with PBS-T for 5 minutes, color was developed by NBT-BCIP solution to confirm expression of recombinant neurosin protein in the culture supernatant.

EXAMPLE 2

Production of Anti-neurosin Polyclonal Antibody (a) Immunization

Purified neruosin protein produced by gene recombinant techniques (100 µg) was mixed with Freund's complete adjuvant, and initial immunization of rabbits was carried out with the mixture. Then, booster immunization was carried out at 2 week intervals according to the same immunization manner. In all, four booster immunizations were carried out.

(b) Purification of Antiserum

Rabbit anti-sera obtained from the rabbits immunized in the above were purified by an affinity column with Sepharose Protein A™ (manufactured by Pharmacia Biotech) to obtain an IgG fraction.

(c) Preparation of Neurosin Antigen Column and Purification of Antibody

An activated affinity carrier resin which had been swollen with water (0.3 g, FMP: 2-fluoro-1-methylpyridinium toluene-4-sulfonate, manufactured by Seikagaku Kogyo) was filled in a column and washed with purified water (10 ml). Purified neurosin protein obtained by gene recombinant techniques (10 µg) was dissolved in a coupling buffer (50 mM sodium carbonate-sodium bicarbonate buffer, pH 8.5). The antigen dissolved in the coupling buffer was filled in the column and both ends of column were sealed with paraffin films. The column was inverted and mixed at 4° C. overnight. Then, the column was washed with the coupling buffer (5 ml). Further, the column was washed with a blocking buffer (20 ml) and the blocking buffer (10 ml) was added to the column. Both ends of the column were sealed with paraffin films and the column was inverted and mixed at room temperature for 3 hours. Then, the column was washed with purified water (20 ml), 1M Gly-HCl (pH 2.5, 20 ml) and then purified water (20 ml). The IgG fraction purified in the above (b) was purified by this neurosin antigen column according to a conventional manner.

EXAMPLE 3

Development of ELISA System Using Anti-neurosin Antibody

The monoclonal antibody obtained in Example 1 was diluted with PBS to concentration of 5 µg/ml. Each 100 µl portion thereof was added to each well of a 96-well plate (manufactured by Corning) and reacted at room temperature for 2 hours. After washing 5 times with purified water, the plate was blocked with a 4-fold dilution of Blockace™ (manufactured by Snow Brand Milk Products) in PBS (300 µl). The blocking solution was discarded, and each 100 µl portion of purified neurosin protein produced by gene recombinant techniques and diluted with PBS at suitable concentration ( 0 to 1,000 ng/ml) was added thereto, followed by reaction at room temperature for 2 hours. After washing 5 times with purified water, the rabbit antiserum obtained in Example 2 was diluted with a serum dilution buffer (PBS containing 5% FBS) at concentration of 5 µg/ml and each 100 µl portion of the dilution was added to each well and the reaction was carried out at room temperature for 2 hours. The plate was washed and then each 100 µl portion of a 2,000-fold dilution of alkaline phosphatase labeled anti-rabbit IgG antibody (manufactured by ICN/Cappl) was added thereto, followed by reaction at room temperature for 1 hour. A substrate solution was prepared by dissolving disodium p-nitrophenylphosphate (SIGMA 104 phosphatase substrate tablets) in a substrate reaction solution (9.6% diethanolamine buffer containing 0.5 mM magnesium chloride, pH 9.7) at concentration of 2 mg/ml. The plate was washed 7 times with purified water and the substrate solution (100 µl/well) was added thereto. After reaction with the substrate solution for 30 minutes, 3 N NaOH (100 µl) was added thereto to stop the reaction and the absorbance was measured at 405 nm.

(b) Influence of Co-existent Materials in Sandwich Enzyme Immunoassay

Influence by human albumin, human immunoglobulin (IgG) and trypsinogen were examined.

According to the same manner as that described with respect to the above ELISA, the same assay was carried out except that, when the reaction with the antigen was carried out, to neurosin protein (200 ng/ml, 50 µl) were added human albumin at suitable concentration (0 to 2,000 µg/ml), human immunoglobulin (IgG) at suitable concentration (0 to 20,000 µg/ml) and trypsinogen at suitable concentration (0 to 40 µg/ml), respectively.

EXAMPLE 4

Figure 2:
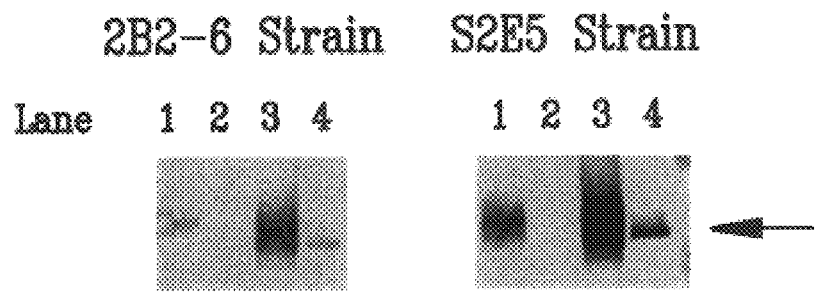
FIG. 2 illustrates comparison of the results of western blotting of the monoclonal antibody of the present invention (electrophoretic photograph).

Measurement of Specimen From Patient (a) Specificity of Monoclonal Antibody For studying specific reactivity of the monoclonal antibodies established by the present invention, 2B2-6 and S2E5 to neurosin, western blotting was carried out. The results are shown in FIG. 2 (electrophoresis pattern). These results show that 2B2-6 and S2E5 recognize recombinant neurosin. Further, it has been found that 2B2-6 and S2E5 have specificity to neurosin because they do not bind to trypsinogen which has high homology to neurosin. In addition, at the same time, a culture supernatant of a naturally occurring pancreas cancer cell strain HPC-Y3 and further cerebrospinal fluid (CSF) were reacted from the viewpoint of a possible difference between recombinant neurosin and naturally occurring one. As a result, bands having the same size were confirmed.

(b) Preparation of Calibration Curve

Figure 3:
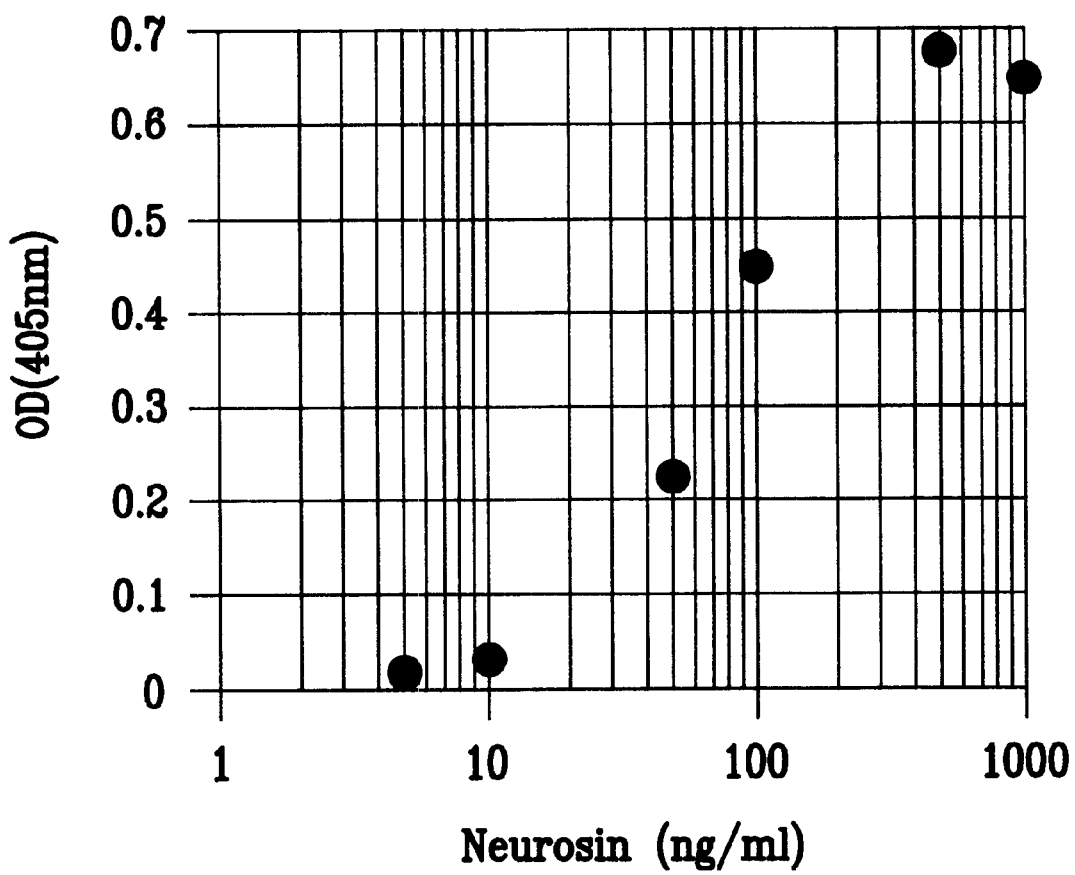
FIG. 3 is a calibration curve of a recombinant neurosin.

While a calibration curve of ELISA can be prepared by the established monoclonal antibody, first, a calibration curve of recombinant neurosin for positive control was prepared. When a calibration curve is good, a sigmoid curve can be obtained. The results are shown in FIG. 3. In FIG. 3, the abscissa represents concentration of neurosin (ng/ml) and the ordinate represents optical density (at 405 nm). As seen from the results, a sigmoid curve was obtained within the neurosin concentration range of 5 to 1,000 ng/ml and linearity was obtained within the range of 10 to 500 ng/ml. Namely, a specimen can be determined quantitatively within this range. Further, sensitivity can be improved by addition of a suitable amount of BSA (e.g., 5 µg/ml).

(c) Study of Influence of Co-existent Material

Figure 4:
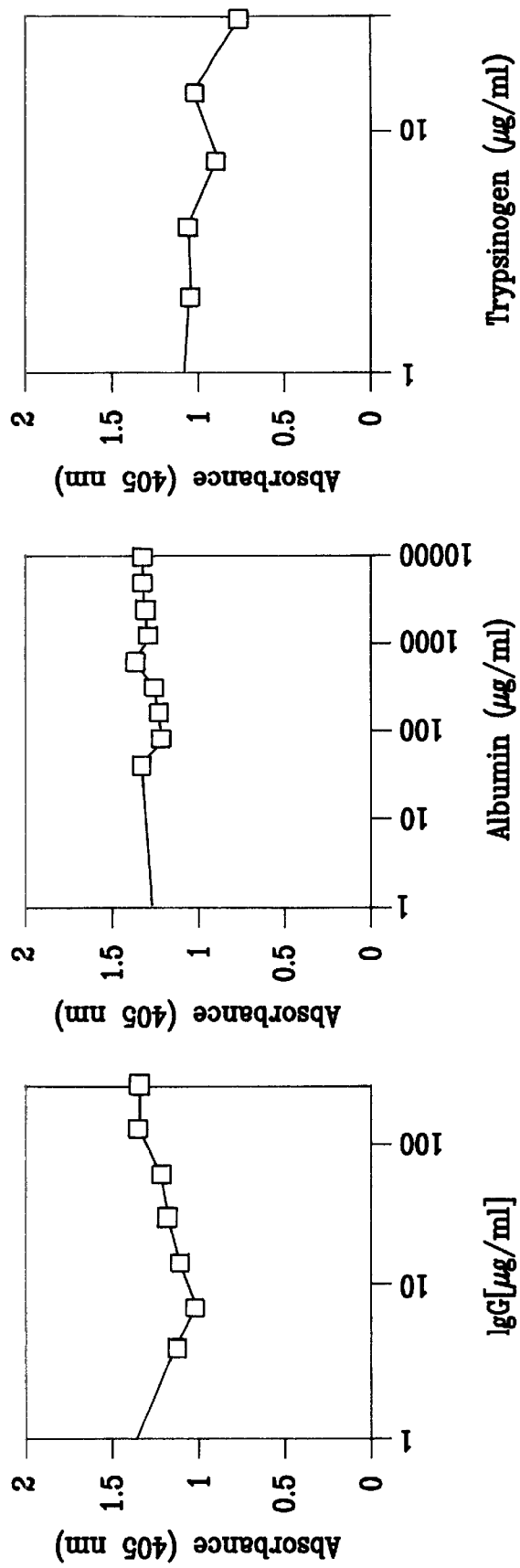
FIGS. 4A, 4B and 4C are graphs illustrating the correlation between concentration of coexisting substances and optical density which shows that coexisting substances have no substantial influence on determination of neurosin by an ELISA system.

In ELISA for determining human samples, there are many co-existent materials which influence on an antigen-antibody reaction. Then, influence of co-existent materials on the assay of the present invention using an ELISA system was studied by using the method described in the above Example 3. Among proteins, albumin and antibodies are considered to cause problems. Then, the quantitative determination was carried out by mixing them with a certain amount of neurosin. Further, although trypsinogen having high homology was also mixed, no influence was recognized. The results are shown in FIGS. 4A to 4C. In these drawings, the abscissas represent concentration (µg/ml) of the co-existent materials, IgG (FIG. 4A), albumin (FIG. 4B) and trypsinogen (FIG. 4C), respectively. The ordinates represent optical density (at 405 nm). As seen from these results, one can understand that a precise amount of neurosin can be determined without substantial influence of co-existent materials by the assay method of the present invention using an ELISA system.

(d) Determination of Neurosin in CSF

Cerebrospinal fluid (CFS) specimens obtained from patients with various diseases including Alzheimer's disease were actually compared with each other by western blotting and ELISA. In ELISA, CFS specimens were diluted ⅒.

The results are shown in FIG. 5 (electrophoresis pattern). As seen from the results, the same results are obtained by western blotting and ELISA. Further, variation is found in the amounts of neurosin in the patient specimens. Therefore, it is possible to prove the relation with each disease by determining the amount of neurosin.

EXAMPLE 5

Purification of Neurosin in CSF (a) Preparation of Antibody Column

The antibody (S2E5, 10 mg) purified by a Protein A column was dialyzed with 0.2 M sodium hydrogen carbonate containing 0.5 M sodium chloride (pH 8.3). The dialyzed antibody was added to a NHS activated Sepharose High Performer™ (Pharmacia) column activated beforehand with 1 mM hydrochloric acid and the reaction was carried out at room temperature for 3 hours. The column was washed with 6-fold volume of a washing solution A (0.5 M ethanolamine solution containing 0.5 M sodium chloride, pH 8.3) and further with 6-fold volume of a washing solution B (0.1 M acetic acid solution containing 0.5 M sodium chloride, pH 4.0). Again, the column was washed with 6-fold volume of the washing solution A and the column filled with the washing solution A allowed to stand at room temperature for 1 hour. Then, the column was washed with 6-fold volume of the washing solution B. Washing with the washing solutions A and B were repeated once and, finally, the column was equilibrated with PBS.

(b) Purification of Neurosin in CSF

After centrifugation of CSF (10 ml) at 15,000 r.p.m. for 20 minutes, the supernatant was dialyzed with PBS. The dialyzed CSF was applied to a S2E5 antibody column which was equilibrated with PBS beforehand. The column was eluted with 5 M sodium thiocyanate and PBS. Then, the eluted fraction was dialyzed with 20 mM MES buffer (pH 6.0). The dialyzed fraction was added to a cation exchange column (High Trap SP™, Pharmacia) which had been equilibrated with 20 mM MES buffer (pH 6.0) beforehand. The column was subjected to gradient elution with sodium chloride (0 to 0.2 M). The all purification steps were carried out at 4° C.

(c) Electrophoresis and Western Blotting of Eluted Fraction

Figure 6:
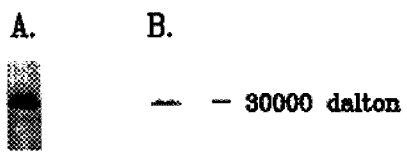
FIG. 6 is electrophoresis patterns of neurosin derived from human CSF and isolated and purified by a cation exchange column.

The fraction eluted with sodium chloride was subjected to SDS-PAGE as shown in Example 1 and the gel was stained by silver staining. Further, electrophoresis was carried out and then, according to the same manner as described above, western blotting was carried out, followed by immunostaining with S2E5 monoclonal antibody used in the antibody column. The results are shown in FIG. 6. As seen from FIG. 6, a single band (A) was detected about a marker of a molecular weight of about 30,000 by silver staining. This band was found in the fraction eluted by about 0.15 M sodium chloride. Further, when this fraction was subjected to immunostaining with S2E5 monoclonal antibody, the same band (B) was detected.

(d) Primary Structure Analysis of Purified CSF-derived Neurosin

The N-terminus amino acid sequence of purified CSF-derived neurosin were analyzed by using an amino acid sequencer (Applied Biosystems, Model 473A). The fraction eluted with 0.15 M sodium chloride was purified by the cation exchange column, concentrated and adsorbed on PVDF membrane with ProSorb™ (Pharmacia) and applied to the amino acid sequencer. As a result, a N-terminus side amino acid sequence was confirmed. The amino acid sequence corresponds to the amino acid sequence of the pro-form deduced from a nucleotide sequence of neurosin. Then, it was found that the monoclonal antibody of the present invention has immunoreactivity with the pro-form of neurosin (FIG. 7). "Neurosin" on FIG. 7, indicates the amino acid sequence for the preproprotein of neurosin as referred to hereinbefore and the amino acid sequence for it from FIG. 7 is designated SEQ ID NO:3. The arrow in FIG. 7 at amino acid 17 (SEQ ID NO:3) indicates the start of the pro-form which is described above. "Mature neurosin" on FIG. 7 has its amino acid sequence set forth in the Sequence Listing as SEQ ID NO:4, and this sequence corresponds to amino acids 22–40 of SEQ ID NO:3. "CSF-derived neurosin" on FIG. 7 means cerebrospinal fluid-derived neurosin and has its amino acid sequence set forth in the Sequence Listing as SEQ ID NO:5; the sequence of SEQ ID NO:5 corresponds to amino acids 17–30 of SEQ ID NO:3.

EXAMPLE 6

Western Blotting of Brain Tissue

Regarding immunological specificity of anti-neurosin antibody, immunoblotting analysis was carried out by using brain tissues obtained from two normal brains and two brains with Alzheimer's disease. Each specimen of the parietal lobe was homogenized with 5-fold volume of a buffer (20 mM Tris-HCl (pH=7.4), 1 mM EGTA, 1 mM EDTA, 10 $\mu$M leupeptin, 1 $\mu$M pepstatin and 0.3 $\mu$M aprotinin) and the homogenate was centrifuged at 15,000 r.p.m. at 4° C. for 30 minutes. The supernatant was collected as a crude cell sol fraction. The precipitate was dissolved again in the homogenization buffer to use as a membrane fraction. A partial specimen containing proteins (50 $\mu$g) from each fraction was subjected to SDS-polyacrylaminde gel (15% polyacrylamide gel) electrophoresis under reduced conditions, followed by transcription on a nitrocellulose membrane by using 25 mM Tris-glycine buffer containing 20% ethanol (pH=8.3). The nitrocellulose membrane used was pre-treated with 25 mM Tris containing 150 mM NaCl (TBS) (pH=7.4) and 5% skimmed milk powder and reacted with the anti-neurosin antibody (2B2-6) diluted to ⅟₁,₀₀₀ with TBS containing 2% skimmed milk powder at 4° C. for 18 hours. The entire membrane was washed with TBS containing 0.1% Tween 20 and reacted with alkaline phosphatase binding anti-mouse antibody in TBST containing 1% skimmed milk at room temperature for 2 hours. Then, the membrane was washed with an alkaline phosphatase substrate buffer (0.1 M Tris-HCl containing 0.33 mg/ml nitroblue tetrazolium (BRL), 0.44 mg/ml 5-bromo-4-chloro-3-indolylphosphoric acid (BRL), 0.1 M NaCl and 50 mM $MgCl_2$).

Figure 8:
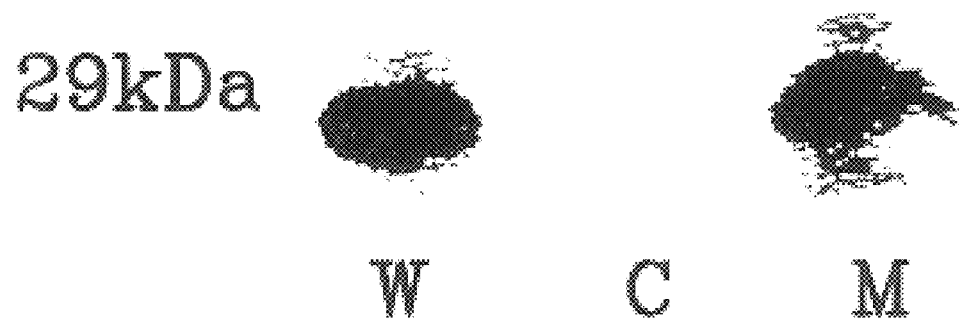
FIG. 8 illustrates the results of immunoblotting analysis using a brain tissue obtained from a neurologically normal patient. Lanes W, C and M are the results obtained by using a homogenate fraction, cytosol fraction and membrane fraction, respectively.

The results are shown in FIG. 8. As seen from FIG. 8, regarding the homogenate fraction (W) and the membrane fraction (M), a single band was confirmed with the anti-neurosin antibody, while it was not observed in the cell sol fraction (c). Therefore, it has been proved that neurosin is present in a membrane fraction in brain tissue.

EXAMPLE 7

Immunostaining of Brain Tissue (a) Preparation of Brain Tissue

Brain tissues were obtained from neurologically normal 7 patients with no Alzheimer's disease, 6 patients with Alzheimer's disease and 5 patients with Parkinson's disease and they were used in this experiment. Alzheimer's disease was diagnosed according to the standard of National Institute on Aging (Khachaturian, Z. S. et al., Arch. Neurol., 42, 1097–1105, 1985). Parkinson's disease was diagnosed according to the standard of Calne et al. (Caine, D. B. et al., Ann. Neurol., 32, S125–127, 1992). The neurologically normal 3 man and 4 women patients were 60 to 82 years old. Two men and 4 women patients with Alzheimer's disease were 67 to 82 years old. Two men and 3 women patients with Parkinson's disease were 70 to 75 years old. Each brain tissue was obtained in 2 to 12 hours after the patient's death.

(b) Immunostaining

Tissue pieces were excised from the respective parietal lobe, hippocampus and midbrain tissues and fixed in a phosphate buffer containing 4% paraformaldehyde for 2 days. Then, they were stored in 0.1 M phosphate buffer containing 15% sucrose (pH=7.4) under low temperature conditions at 4° C. until they were used in the experiment. When using in the experiment, each tissue piece was frozen and sliced in 20 μm thick with a microtome and was stained by immunohistological techniques (McGeer, P. L. et al., Can. J. Neurol. Sci., 16, 516–526, 1989). The anti-neurosin antibody (S2E5) was diluted 1/1,000-fold and the primary antibody and the tissue slice were reacted at low temperature for 48 hours, followed by washing with PBS containing 0.3% Triton X-100 (PBST). Then, it was further reacted with avidin-biotin HRP complex (Vector), followed by further reaction with biotin binding anti-mouse IgG antibody (Vector) at room temperature for 2 hours. After washing with PBST, the peroxidase label was visualized with a solution containing 0.001% 3,3'-diaminobenzidine, 0.6% ammonium nickelosulfate, 0.05% imidazole and 0.0003% $H_2O_2$. When dark purple color development was observed, the reaction was stopped. The slice was washed, mounted on a glass slide, dehydrated with alcohol and then protected with enteran.

(c) Results

The results obtained by using the brain tissues of the patients with Alzheimer' disease are shown in FIGS. 9C–9F and those obtained by the brain tissues of the patients with Parkinson's disease are shown in FIGS. 10C–10F.

Figure 9:
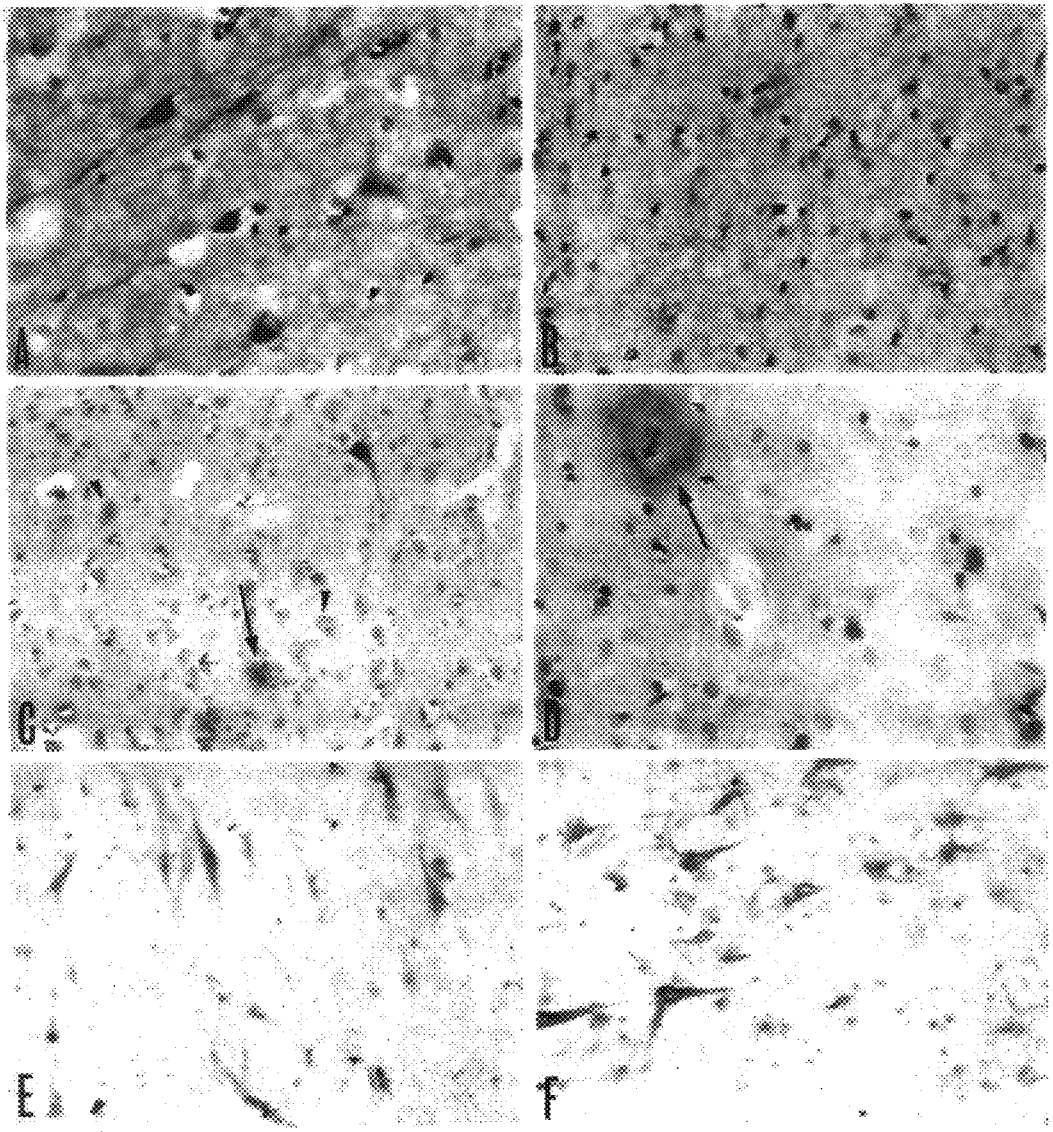
FIGS. 9A–9F illustrate the results of immunostaining of brain tissues with an anti-neurosin antibody.

In immunohistochemical staining with the anti-neurosin antibody, all nuclei of neurons in brain used a control were stained (FIG. 9). And, the other neuron components such as nucleoli, axons and cytoplasm were also stained (FIGS. 9A and 9B). The similar results were obtained with respect to staining of nuclei in all the brains used in the experiment.

In the brains of the patients with Alzheimer's disease, the neurons having axons were scarcely stained in the damaged region such as parietal lobe (FIG. 9C) and hippocampus CA1 region (FIG. 9F). Only nuclei of neurons were stained in this region. However, all the components of neuron were clearly stained in hippocampus CA4 region (FIG. 9E). Several senile plaques were stained (FIGS. 9C and 9D) and the extracellular nerve fibril change region was also neurosin positive (FIG. 9F). Intracellular nerve fibril change region was neurosin negative. In the midbrain tissue of the patients with Parkinson's disease, all neurons in oculomotor nucleus were neurosin positive (FIG. 10A). In the control brain, several nerve cells containing melanin in nigra were neurosin positive (FIG. 10B). In the brain with Parkinson's disease, neuron being neurosin positive and containing melanin was scarcely observed (FIG. 10C). Lewy bodies were neurosin positive (FIG. 10D).

Figure 10:
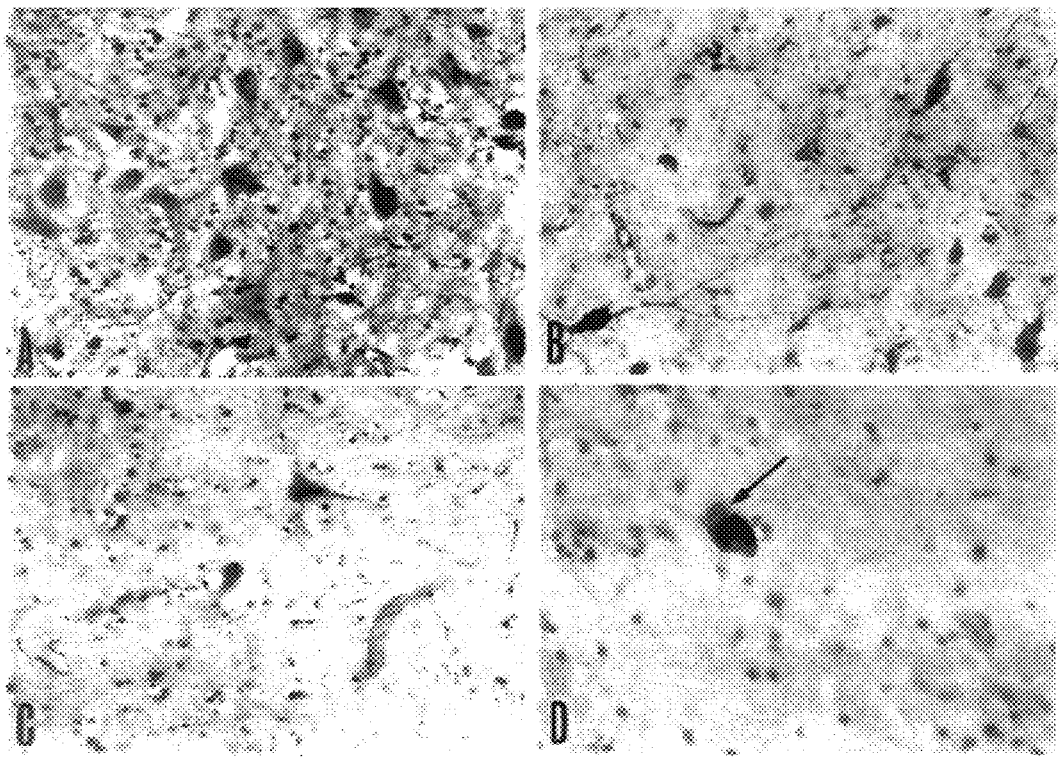
FIGS. 10A–10D illustrate the results of immunostaining of brain tissues with anti-neurosin antibody.

As seen from FIGS. 9 and 10, among the brain tissues of the patients with Alzheimer's disease, Parkinson's disease and the normal patients, the results of immunostaining with the anti-neurosin antibody are different from one another. Then, these disease can be diagnosed by an immunohistological test.

EXAMPLE 8

Improvement of ELISA (a) Improved ELISA (Sandwich Method)

The monoclonal antibody (S2E5) obtained in Example 1 was diluted to 5 μg/ml with PBS. Each 100 μl portion thereof was added to each well of a 96-well plate (manufactured by Corning), followed by reaction at room temperature for 2 hours. After washing with PBS 5 times, the plate was blocked with a 4-fold dilution of Blockace™ (manufactured by Snow Brand Milk Products) in PBS (300 μl). The blocking solution was discarded and, again, washed with PBS containing 0.05% Tween 20™ (PBS-T). Then, the recombinant neurosin protein produced and purified in Example 1 was diluted with PBS containing 0.5% BSA (PBS-B) to suitable concentration (0 to 1,000 ng/ml). Each 100 μl portion thereof was added to each well, followed by reaction at room temperature for 2 hours. After washing 5 times with PBS-T, each 100 μl portion of the antiserum obtained in Example 2 and diluted to 5 μg/ml with PBS-B was added to each well, followed by reaction at room temperature for 2 hours. After washing the plate with PBS-T, each 100 μl portion of a 5,000-fold dilution of alkaline phosphatase labeled anti-rabbit IgG antibody (manufactured by Biochem) in PBS-B was added to each well, followed by reaction at room temperature for 1 hour. Disodium p-nitrophenylphosphate (SIGMA 104 phosphatase substrate tablets) was dissolved in a substrate reaction mixture (9.6% diethanolamine buffer containing 0.5 mM magnesium chloride, pH 9.7) at concentration of 2 mg/ml to prepare a substrate solution. The plate was washed 7 times with PBS-T and the substrate solution (100 μl/well) was added to the plate. After reaction with the substrate solution for 20 minutes, 3N NaOH (100 μl) was added to stop the reaction and the absorbance at 405 nm was measured.

Figure 11:
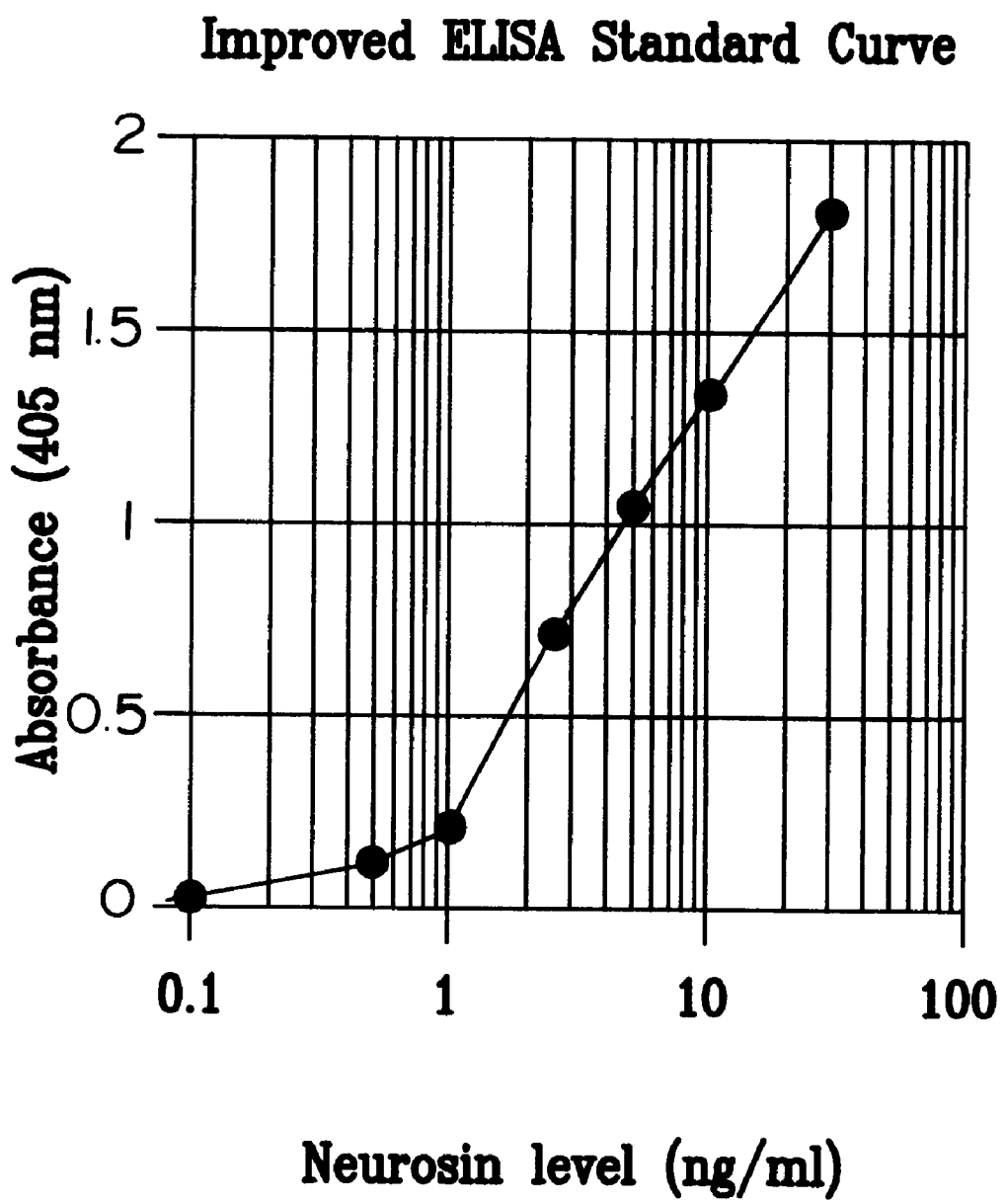
FIG. 11 is an improved ELISA standard curve.

The ELISA standard curve after improvement is shown in FIG. 11. In FIG. 11, the abscissa represents concentration of neurosin (ng/ml) and the ordinate represents optical density (at 405 nm). As seen from these results, linearity was obtained in the neurosin concentration range of 1 to 30 ng/ml and sensitivity was significantly increased by using the above improved ELISA.

(b) Measurement of Serum Neurosin

Figure 12:
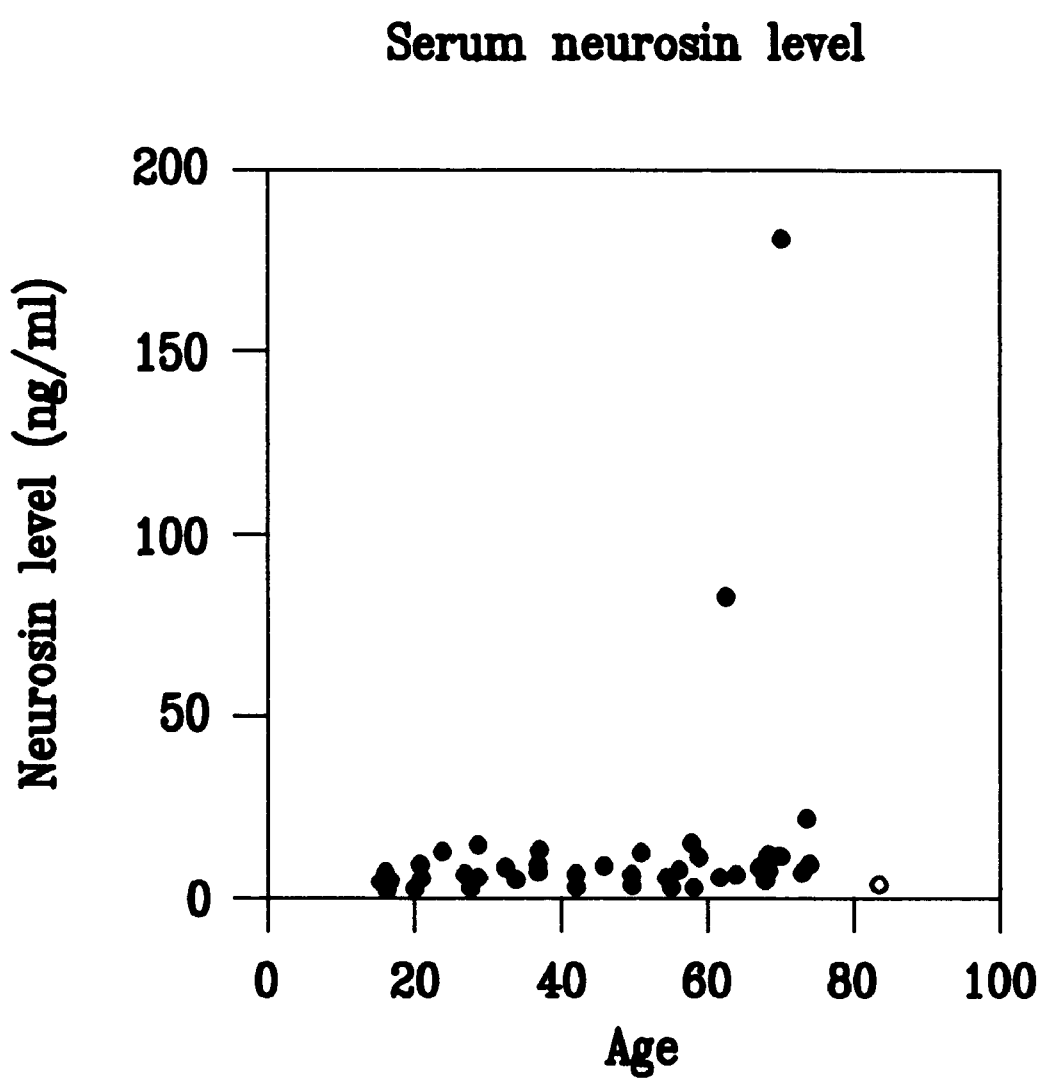
FIG. 12 is serum neurosin level determined by the improved ELISA.

Serum neurosin levels of normal persons and patients (with Alzheimer's disease, Parkinson's disease and other various diseases) were measured by the above improved ELISA. In ELISA, the serum was diluted to 1/200 and subjected to the measurement. As a result, it was found that serum neurosin level could be measured with high sensitivity even at concentration of 80 ng/ml by using the ELISA experimental system. As seen from FIG. 12, among 50 specimens measured, 48 specimens scarcely contained neurosin in the sera, while 2 specimens had high serum neurosin levels.

(c) Correlation Between Various Diseases and Neurosin Level in CSF

Neurosin level in CSF of a patient was measured by the above ELISA. As a result, CSF neurosin level of a patient of a peripheral nerve disease different from a central nervous disease (a control group for central nervous diseases) was increased as the patient became older. And, dementia of central nervous diseases was divided into three groups, i.e., degenerative dementia, vascular dementia and Alzheimer type dementia and their CSF neurosin levels were measured. As a result, in degenerative dementia group, similarly to the control group, as CSF neurosin level was increased as the patient became older and was distributed in the higher concentration zone. On the other hand, in vascular dementia group, no correlation between age and CSF neurosin level was observed. In particular, CSF neurosin level of a patient with Alzheimer's disease was distributed in the lower concentration zone. This result supports the results of tissue immunostaining.

As described hereinabove, according to the present invention, the monoclonal antibody having specificity to neurosin is provided. The anti-neurosin antibody of the present invention makes it possible to detect neurosin in a sample (e.g., CSF).

Further, the monoclonal antibody of the present invention does not show any cross reactivity with IgG, albumin and trypsinogen which are considered to be contaminants in a specimen or sample. Then, an ELISA system having good sensitivity can be established.

It can be said that novel diagnosis has been established by the present invention because a neurosin level relates to various diseases.

Furthermore, for example, brain slices can be stained by immunostaining using the anti-neurosin antibody of the present invention. Then, it makes possible to analyze various diseases immunohistologically.

Sequence Listing Free Text

SEQ ID NO: 1
Designed oligonucleotide primer to amplify neurosin gene.

SEQ ID NO: 2
Designed oligonucleotide primer to amplify neurosin gene.

What is claimed is:

1. A hybridoma which is hybridoma cell line 2B2-6 deposited as Accession No. FERM BP-7341.

2. A hybridoma which is hybridoma cell line S2E5 deposited as Accession No. FERM BP-7342.

3. A monoclonal antibody against neurosin and/or a precursor of neurosin which is produced by the hybridoma according to claim 1 and does not show cross-reactivity with IgG, albumin and trypsinogen.

4. A monoclonal antibody against neurosin and/or a precursor of neurosin which is produced by the hybridoma according to claim 2 and does not show cross-reactivity with IgG, albumin and trypsinogen.

5. A method for quantitative determination of neurosin and/or precursor of neurosin contained in a sample, comprising immunoreacting neurosin and/or precursor of neurosin in the sample with the antibody according to claim 3 or 4, said antibody being labeled and determining an amount of a labeled immunoreaction product.

6. The method according to claim 5 wherein the determination method comprises ELISA with the labeled antibody being enzyme-linked antibody.

7. An immunohistological test method for determining presence or amount of neurosin and/or precursor of neurosin in a tissue sample, comprising immunoreacting the antibody according to claim 3 or 4 with the tissue sample and then further reacting to develop a visually observable color if immunoreaction product is present indicative of the presence or amount of neurosin and/or precursor of neurosin in the tissue sample.

8. An immunohistological test method for diagnosing Alzheimer's disease in a patient comprising:
  (a) preparing a brain tissue sample from a patient to be tested and a neurologically normal brain tissue sample;
  (b) immunoreacting each of the samples with the antibody according to claim 3 or 4 separately to develop a visually observable immunoreaction result indicative of a level and/or distribution of neurosin and/or precursors of neurosin in each of the samples;
  (c) comparing the immunoreaction results between the separate samples; and
  (d) determining the patient as with Alzheimer's disease when the result of the immunoreaction of the sample from the patient indicates a different level and/or distribution of neurosin and/or precursors of neurosin from that from the neurologically normal brain tissue sample.

9. An immunohistological test method for diagnosing Parkinson's disease in a patient comprising:
  (a) preparing a brain tissue sample from a patient to be tested and a neurologically normal brain tissue sample;
  (b) immunoreacting each of the samples with the antibody according to claim 3 or 4 separately to develop a visually observable immunoreaction result indicative of a level and/or distribution of neurosin and/or precursors of neurosin in each of the samples;
  (c) comparing the immunoreaction results between the separate samples; and
  (d) determining the patient as with Parkinson's disease when the result of the immunoreaction of the sample from the patient indicates a different level and/or distribution of neurosin and/or precursors of neurosin from that from the neurologically normal brain tissue sample.

10. A method for diagnosing Alzheimer's disease in a patient comprising measuring a concentration of neurosin and/or precursor of neurosin in a brain tissue sample or a cerebrospinal fluid (CSF) sample from the patient by quantitatively detecting immunoreaction with the antibody according to claim 3 or 4, and diagnosing whether Alzheimer's disease is present in the patient by comparing measurement results to standards correlating Alzheimer's disease presence with a concentration of neurosin and/or precursor of neurosin in that kind of a brain tissue sample or a CSF sample.

11. A method for diagnosing Parkinson's disease in a patient comprising measuring a concentration of neurosin and/or precursor of neurosin in a brain tissue sample or a cerebrospinal fluid (CSF) sample from the patient by quantitatively detecting immunoreaction with the antibody according to claim 3 or 4, and diagnosing whether Parkinson's disease is present in the patient by comparing measurement results to standards correlating Parkinson's disease presence with a concentration of neurosin and/or precursor of neurosin in that kind of a brain tissue sample or a CSF sample.

12. A composition for determining a neurosin and/or precursor of neurosin immunoreaction which comprises the monoclonal antibody according to claim 3 diluted with buffer solution.

13. A composition for determining a neurosin and/or precursor of neurosin immunoreaction which comprises the monoclonal antibody according to claim 4 diluted with buffer solution.

* * * * *

SEQUENCE LISTING

```
<160> NUMBER OF SEQ ID NOS:  5

<210> SEQ ID NO 1
<211> LENGTH: 27
<212> TYPE: DNA
<213> ORGANISM: Artificial Sequence
<220> FEATURE:
<221> NAME/KEY: misc_feature
<223> OTHER INFORMATION: Designed oligonucleotide primer to amplify
      neurosin gene

<400> SEQUENCE: 1
cgcggatcct tggtgcatgg cggaccc                                        27

<210> SEQ ID NO 2
<211> LENGTH: 27
<212> TYPE: DNA
<213> ORGANISM: Artificial Sequence
<220> FEATURE:
<221> NAME/KEY: misc_feature
<223> OTHER INFORMATION: Designed oligonucleotide primer to amplify
      neurosin gene

<400> SEQUENCE: 2
cgcggatcct cacttggcct gaatggt                                        27

<210> SEQ ID NO 3
<211> LENGTH: 40
<212> TYPE: PRT
<213> ORGANISM: Human being

<400> SEQUENCE: 3

Met Lys Lys Leu Met Val Val Leu Ser Leu Ile Ala Ala Ala Trp Ala
1               5                   10                  15

Glu Glu Gln Asn Lys Leu Val His Gly Gly Pro Cys Asp Lys Thr Ser
            20                  25                  30

His Pro Tyr Gln Ala Ala Leu Tyr
        35                  40

<210> SEQ ID NO 4
<211> LENGTH: 19
<212> TYPE: PRT
<213> ORGANISM: Human being

<400> SEQUENCE: 4

Leu Val His Gly Gly Pro Cys Asp Lys Thr Ser His Pro Tyr Gln Ala
1               5                   10                  15

Ala Leu Tyr

<210> SEQ ID NO 5
```

```
<211> LENGTH: 14
<212> TYPE: PRT
<213> ORGANISM: Human being

<400> SEQUENCE: 5

Glu Glu Gln Asn Lys Leu Val His Gly Gly Pro Cys Asp Lys
1               5                   10
```